United States Patent
Barabas et al.

(10) Patent No.: US 9,850,464 B2
(45) Date of Patent: Dec. 26, 2017

(54) METHOD FOR THE DETECTION OF POLYPEPTIDE SPECIFIC IMMUNE CELLS

(71) Applicant: LOPHIUS BIOSCIENCES GMBH, Regensburg (DE)

(72) Inventors: Sascha Barabas, Bad Abbach (DE); Katrin Edmaier-Schröger, Planegg (DE); Ludwig Deml, Regenstauf (DE)

(73) Assignee: LOPHIUS BIOSCIENCES GMBH, Regensburg (DE)

(*) Notice: Subject to any disclaimer, the term of this patent is extended or adjusted under 35 U.S.C. 154(b) by 0 days.

(21) Appl. No.: 15/260,269

(22) Filed: Sep. 8, 2016

(65) Prior Publication Data

US 2017/0058260 A1  Mar. 2, 2017

Related U.S. Application Data

(62) Division of application No. 13/263,641, filed as application No. PCT/EP2010/054711 on Apr. 9, 2010, now Pat. No. 9,476,878.

(30) Foreign Application Priority Data

Apr. 9, 2009 (EP) .................................. 09157777

(51) Int. Cl.
*A61K 39/00* (2006.01)
*C12N 5/00* (2006.01)
*A61K 38/00* (2006.01)
*C12N 5/0783* (2010.01)
*G01N 33/569* (2006.01)

(52) U.S. Cl.
CPC ..... *C12N 5/0636* (2013.01); *G01N 33/56972* (2013.01)

(58) Field of Classification Search
None
See application file for complete search history.

(56) References Cited

U.S. PATENT DOCUMENTS

| | | | |
|---|---|---|---|
| 5,075,110 | A | 12/1991 | Francon et al. |
| 5,639,854 | A | 6/1997 | Sia et al. |
| 6,977,073 | B1 | 12/2005 | Cezayirli et al. |
| 7,829,331 | B2 | 11/2010 | Wolf et al. |
| 2006/0057108 | A1 | 3/2006 | Wolf et al. |
| 2011/0053828 | A1 | 3/2011 | Wolf et al. |

FOREIGN PATENT DOCUMENTS

| | | |
|---|---|---|
| EP | 0 421 949 | 4/1991 |
| GB | 1 128 005 | 9/1968 |
| WO | WO 03/080792 | 10/2003 |
| WO | WO 2008/101680 | 8/2008 |
| WO | WO 2009/153750 | 12/2009 |

OTHER PUBLICATIONS

Wang et al., "Protein carbamylation links inflammation, smoking, uremia and atherogenesis," *Nature Medicine*, 13(10):1176-1184, 2007.

"Liquor" Stedmans Medical Dictionary 27th Edition, 2000.
Angel et al., "Quantitative carbamylation as a stable isotopic labeling method for comparative proteomics," *Rapid Commun. Mass Spectrom.*, 21(10):1623-1634, 2007.
Anonymous, "Carbamylation of proteins," Ionsource.com. Online. Feb. 17, 2007. Retrieved from the Internet: http://www.ionsource.com/Card/carbam/carbam.htm, retrieved Aug. 26, 2009.
Barabas et al., "Urea-mediated cross-presentation of soluble Epstein-ban virus BZLF1 protein," *PLOS Pathogens*, 4(11):1-10, 2008.
Bauer et al., "Induction of MHC class-I and -II restricted epitope presentation by urea-treated BZLF1 protein: a novel technology for the detection of protein-specific cytotoxic t-cells," *Proceedings of the EBV2002 Conference*, p. 34, 2002.
Broff et al., "Nature of the immunogenic moiety recognized by the human T cell proliferating in response to tetanus toxoid antigen," *Eur. J. Immunol.*, 11:365-71, 1981.
Carbone et al., "Induction of cytotoxic T lymphocytes by primary in vitro stimulation with peptides," *J. Exp. Med.*, 167:1767-1779, 1988.
Cheng et al., "Role of lipid trimming and CD1 groove size in cellular antigen presentation," *The EMBO Journal*, 25(13): 2989-2999, 2006.
Dempster et al., "Parasite vaccine development: large-scale recovery of immunogenic Taenia ovis fusion protein GST-45W(B/X) from *Escherichia coli* inclusion bodies," 82(4):291-296, 1996.
Dirnhuber et al., "The isomeric transformation of urea into ammonium cyanate in aqueous solutions," *Biochemical Journal*, 42(4):628-632, 1948.
Doucett et al., "Enumeration and characterization of virus-specific B cells by multicolor flow cytometry," *J. Immunol. Methods*, 303:40-52, 2005.
Elliot et al., "Dominant cytotoxic T Lymphocyte response to the immediate-early trans-activator protein, BZLF1, in persistent type A or B Epstein-Barr virus infection," *Journal of Infectious Diseases*, 176:1068-1072, 1997.
Grimaldi et al., "Monoclonal antibodies by somatic cell fusion," *ILAR Journal*, V37(3):1-7, 1995.
Halthman et al., "The effect of cyanate on the stability of proteins," *Biochimica et Biophysica Acta*, 3: 65-81, 1949. (Abstract only).
Herr et al., "Mature dendritic cells pulsed with freeze-thaw cell lysates define an effective in vitro vaccine designed to elicit EBV-specific CD4(+) and CD8(+) T lymphocyte responses," *Blood*, 96(5):18571864, 2000.
Higgins et al., "TLR, NLR Agonists, and Other Immune Modulators as Infectious Disease Vaccine Adjuvants," *Curr. Infect. Dis. Rep.*, 12(1):4-12, 2010.
Hodge et al., "Oligomerization of the HIV type 2 Nef protein: mutational analysis of the heptad leucine repeat motif and cysteine residues," *AIDS Res. And Human Retro*, 11(1):65-79, 1995.
Invitrogen Technical Resources—Media Formulations, pp. 1-3, 2008.
Jenne et al., "Viral vectors for dendritic cell-based immunotherapy," *Trends Immunol.*, 22(2):102-107, 2001.
Kanesa-thasan et al., "Safety and immunogenicity of attenuated dengue virus vaccines (Aventis Pasteur) in human volunteers," *Vaccine*, 3179-3188, 2001.

(Continued)

*Primary Examiner* — Michail Belyavskyi
(74) *Attorney, Agent, or Firm* — Parker Highlander PLLC

(57) ABSTRACT

The present invention relates to a method for polypeptide transfer into cells. The present invention further relates to the detection of polypeptide-specific immune cells and the priming, expansion and reactivation of polypeptide-specific T cells. Moreover the present invention relates to polypeptides of the methods of the present invention in combination with urea and their use for research, diagnosis or treatment and prevention of diseases in animals and humans.

22 Claims, 23 Drawing Sheets

(56) References Cited

OTHER PUBLICATIONS

Kerblat et al., "Tetanus toxin L chain is processed by major histocompatibility complex class I and class II pathways and recognized by CD8+ or CD4+ T lymphocytes," *Immunology*, 100(2):178-184, 2000.

Kessler et al, "Measurement of Urea in Human Serum by Isotope Dilution Mass Spectrometry: A Reference Procedure," *Clinical Chemistry*, 45:1523-1529, 1999.

Kraus et al., "Carbamoylation of amino acids and proteins in uremia," *Kidney International*, 59(78):S102-S107, 2001.

Lippincott and Apostol, "Carbamylation of cysteine: a potential artifact in peptide mapping of hemoglobins in the presence of urea", *Analytical Biochemistry*, 267:57-64, 1999.

Marier et al., "Determination of cyanate, and a study of its accumulation in aqueous solutions of urea," *Analytical Biochemistry*, 7:304-314, 1964.

Mi et al., "Characterization of a class of cationic peptides able to facilitate efficient protein transduction in vitro and in vivo," *Mol. Ther.* 2(4):339-347, 2000.

Nagahara et al., "Transduction of full-length TAT fusion proteins into mammalian cells: TAT-p27Kip1 induces cell migration," *Nat. Med.*, 4:1449-1452, 1998.

O'Hagan et al., "Recent developments in adjuvants for vaccines against infectious diseases," *Biomol. Engin.*, 18:69-85, 2001.

Office Communication issued in U.S. Appl. No. 12/873,966, dated Sep. 18, 2012.
Office Communication issued in U.S. Appl. No. 12/873,966, dated May 10, 2012.
Office Communication issued in U.S. Appl. No. 12/873,966, dated Mar. 5, 2012.
Office Communication issued in U.S. Appl. No. 12/873,966, dated Oct. 27, 2011.
Office Communication issued in U.S. Appl. No. 12/873,966, dated May 12, 2011.
Office Communication issued in U.S. Appl. No. 12/873,966, dated Feb. 18, 2011.
Office Communication, issued in U.S. Appl. No. 10/508,642, dated Sep. 15, 2009.
Office Communication, issued in U.S. Appl. No. 10/508,642, dated Apr. 6, 2009.
Office Communication, issued in U.S. Appl. No. 10/508,642, dated Jul. 23, 2008.
Office Communication, issued in U.S. Appl. No. 10/508,642, dated Oct. 18, 2007.
Office Communication, issued in U.S. Appl. No. 10/508,642, dated Mar. 23, 2007.
Office Communication, issued in U.S. Appl. No. 10/508,642, dated Sep. 25, 2006.
Office Communication, issued in U.S. Appl. No. 10/508,642, dated Apr. 10, 2006.
Office Communication, issued in U.S. Appl. No. 10/508,642, dated Jan. 11, 2006.
Office Communication, issued in U.S. Appl. No. 13/263,641, dated Oct. 25, 2013.
Office Communication, issued in U.S. Appl. No. 13/263,641, dated Mar. 4, 2014.
Office Communication, issued in U.S. Appl. No. 13/263,641, dated Jan. 7, 2015.
Office Communication, issued in U.S. Appl. No. 13/263,641, dated May 22, 2015.
Office Communication, issued in U.S. Appl. No. 13/263,641, dated Jul. 9, 2015.

Pala et al., "Flow cytometric measurement of intracellular cytokines," *J. Immunol. Methods*, 243:107-24, 2000.

PCT International Preliminary Report on Patentability issued in International application No. PCT/EP2010/054711, dated Oct. 20, 2011.

PCT International Search Report and Written Opinion issued in International application No. PCT/EP2010/054711, dated Jul. 30, 2010.

Petersen et al., "Phosphorylated self-peptides alter human leukocyte antigen class I-restricted antigen presentation and generate tumor-specific epitopes," *PNAS*, 106(8):2776-2781, 2009.

Prabhakar et al., "Urea inhibits inducible nitric oxide synthase in macrophage cell line," *Am. J. Phys.*, 273:1882-1888, 1997.

Rodriguez et al., "DNA immunization: ubiquitination of a viral protein enhances cytotoxic T-lymphocyte induction and antiviral protection but abrogates antibody induction," *Journal of Virology*, 71(11): 8497-8503, 1997.

Rothel et al., "Urea/DTT solubilization of a recombinant Taenia ovis antigen, 45W, expressed as a GST fusion protein results in enhanced protective immune response to the 45W moiety," *Vaccine*, 15(5):469-472, 1997.

Schenk et al., "T-cell epitopes of Phl p 1, major pollen allergen of timothy grass (*Phleum pratense*): evidence for crossreacting and non-crossreacting T-cell epitopes within grass group I allergens," *J. Allergy Clin. Immunol.*, 96:986-996, 1995.

Schirmbeck et al., "Injection of detergent-denatured ovalbumin primes murine class I-restricted cytotoxic T cells in vivo," *Eur. J. Immunol.*, 24(9):2068-2072, 1994.

Schirmbeck et al., "Injection of detergent-denatured ovalbumin primes murine class I-restricted cytotoxic T cells in vivo," *Eur. J. Immunol.*, 24:2068, 1994.

Schirmbeck et al., "Priming of class I-restricted cytotoxic T lymphocytes by vaccination with recombinant protein antigens," *Vaccine*, 13(9):857, 1995.

Schwarze et al., "Protein transduction: unrestricted delivery into all cells?" *Trends Cell* Biol. 10:290, 2000.

Sester et al., "Rapid whole blood analysis of virus-specific CD4 and CD8 T cell responses in persistent HIV infection," *AIDS*, 14:2653-60, 2000.

Sheil et al., "Identification of an autologous insulin B chain peptide as a target antigen for H-2Kb-restricted cytotoxic T lymphocytes," *J. Exp. Med.*, 175:545-552, 1992.

Sone et al., "T cell epitopes in Japanese cedar (*Cryptomeria japonica*) pollen allergens: choice of major T cell epitopes in Cry j 1 and Cry j 2 toward design of the peptide-based immunotherapeutics for the management of Japanese cedar pollinosis," *J. Immunol.*, 161:448-457, 1998.

Stack et al.,"A ubiquitin-based tagging system for controlled modulation of protein stability," *Nature Biotechnolgy*, 18:1298-1302, 2000.

Suni et al., "$CD4^+CD8^{dim}$ T lymphocytes exhibit enhanced cytokine expression, proliferation and cytotoxic activity in response to HCMV and HIV-1 antigens," *Eur. J. Immunol.*, 31:2512-2520, 2001.

Van Kaer et al., "Innate immunity: NKT cells in the spotlight," *Curr. Biol.*, 15:R429-31, 2005.

Van Rhijn et al., "T-cell activation by lipopeptide antigens," *Current Opinion in Immunology*, 17:222-229, 2005.

Venkatesu et al., "Osmolyte counteracts urea-induced denaturation of α-chymotrypsin," *J. Phys. Chem. B*, 113:5327-5338, 2009.

Wild et al., "Influence of polypeptide size and intracellular sorting on the induction of epitope-specific CTL responses by DNA vaccines in a mouse model," *Vaccine*, 22(13-14):1732-1743, 2004.

FIG. 1

Decomposition of urea

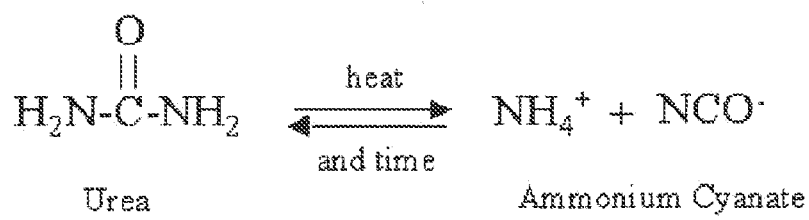

Urea ⇌ (heat and time) NH$_4^+$ + NCO$^-$ (Ammonium Cyanate)

Carbamoylation of proteins
amino terminus of a peptide used as an example

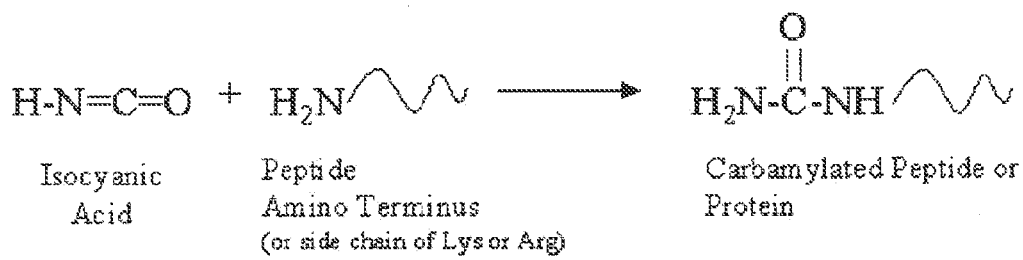

Isocyanic Acid + Peptide Amino Terminus (or side chain of Lys or Arg) → Carbamylated Peptide or Protein

| Amino Acid | Residue Composition | Residue Monoisotopic Mass | Delta Mass |
|---|---|---|---|
| Lysine | C$_6$H$_{12}$N$_2$O | 128.09496 | 0 |
| Carbamoyl Lysine | C$_7$H$_{13}$N$_3$O$_2$ | 171.10078 | 43.00582 |
| Carbamoylation | * NHCO | 43.00582 | - |

*Note: A proton is lost from the amino group on the protein during carbamoylation and thus the change in composition is NHCO.

ionsource.com/Card/carbam/carbam.htm

Christison et al, "Direct Determination of Cyanate in a Urea Solution and a Urea Containing Protein Buffer Using a Reagent-Free Ion Chromatography System", Dionex (www.dionex.com)

FIG. 6A-C

FIGS. 8A-D
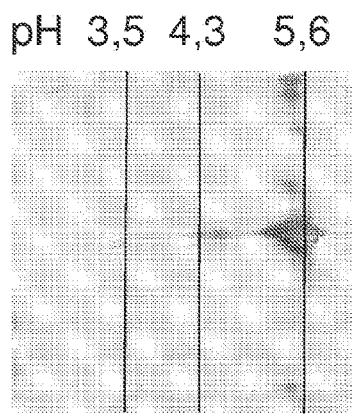
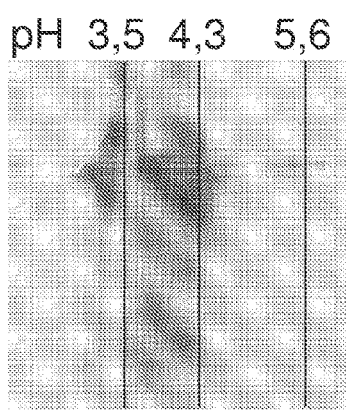
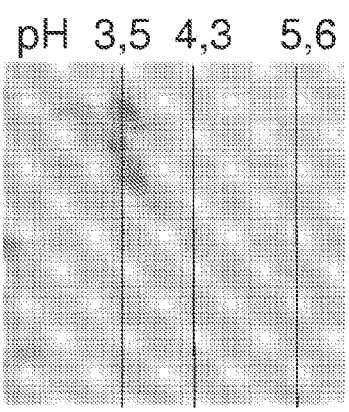

FIGS. 10A-B
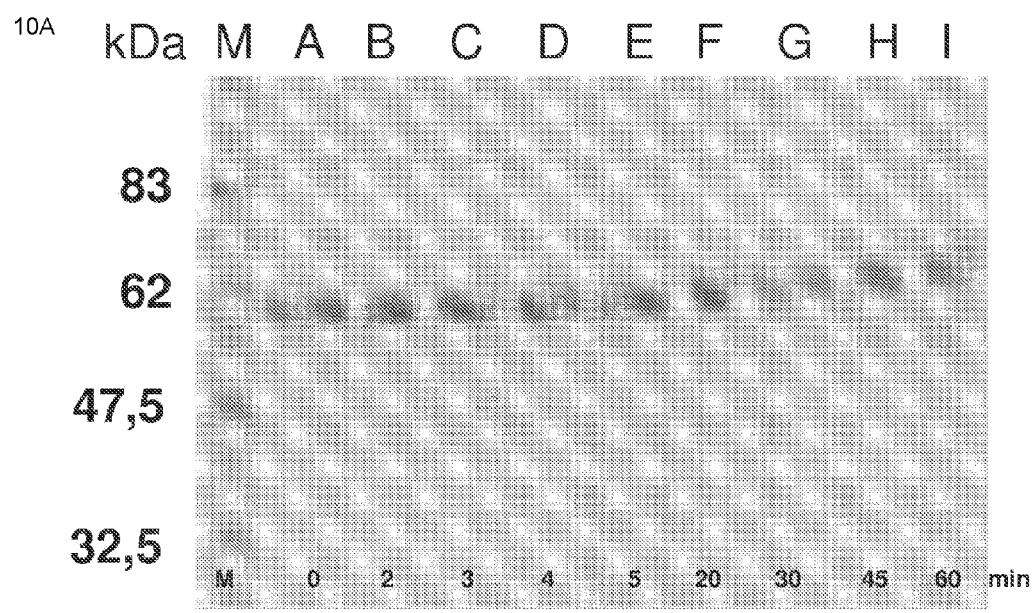
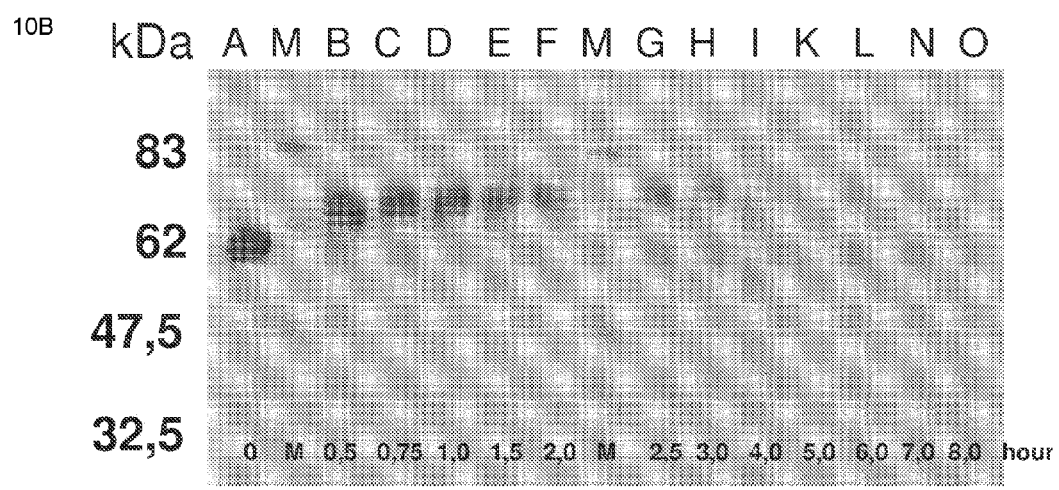

FIGS. 12A-B
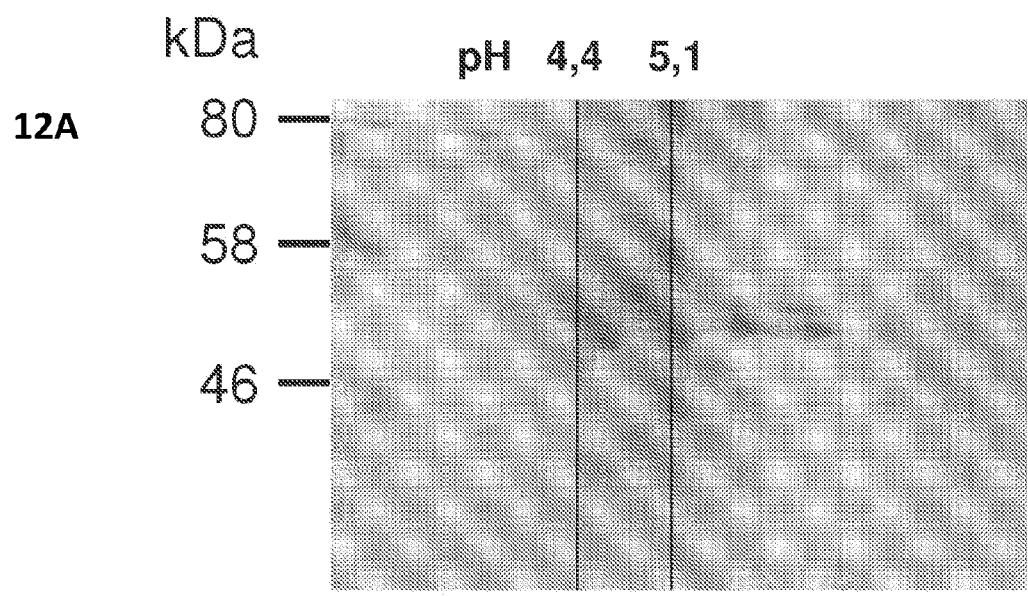
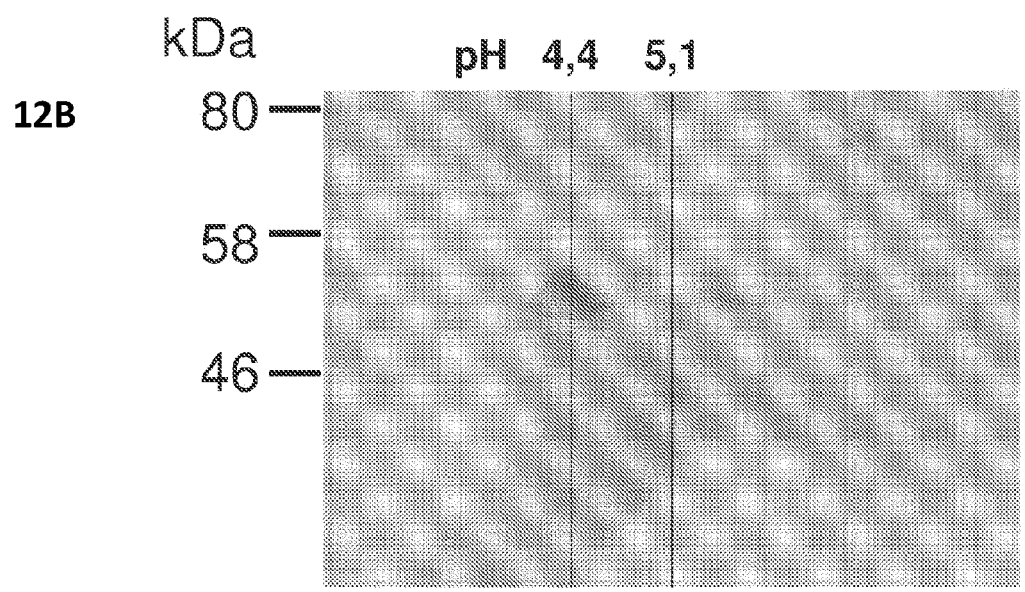

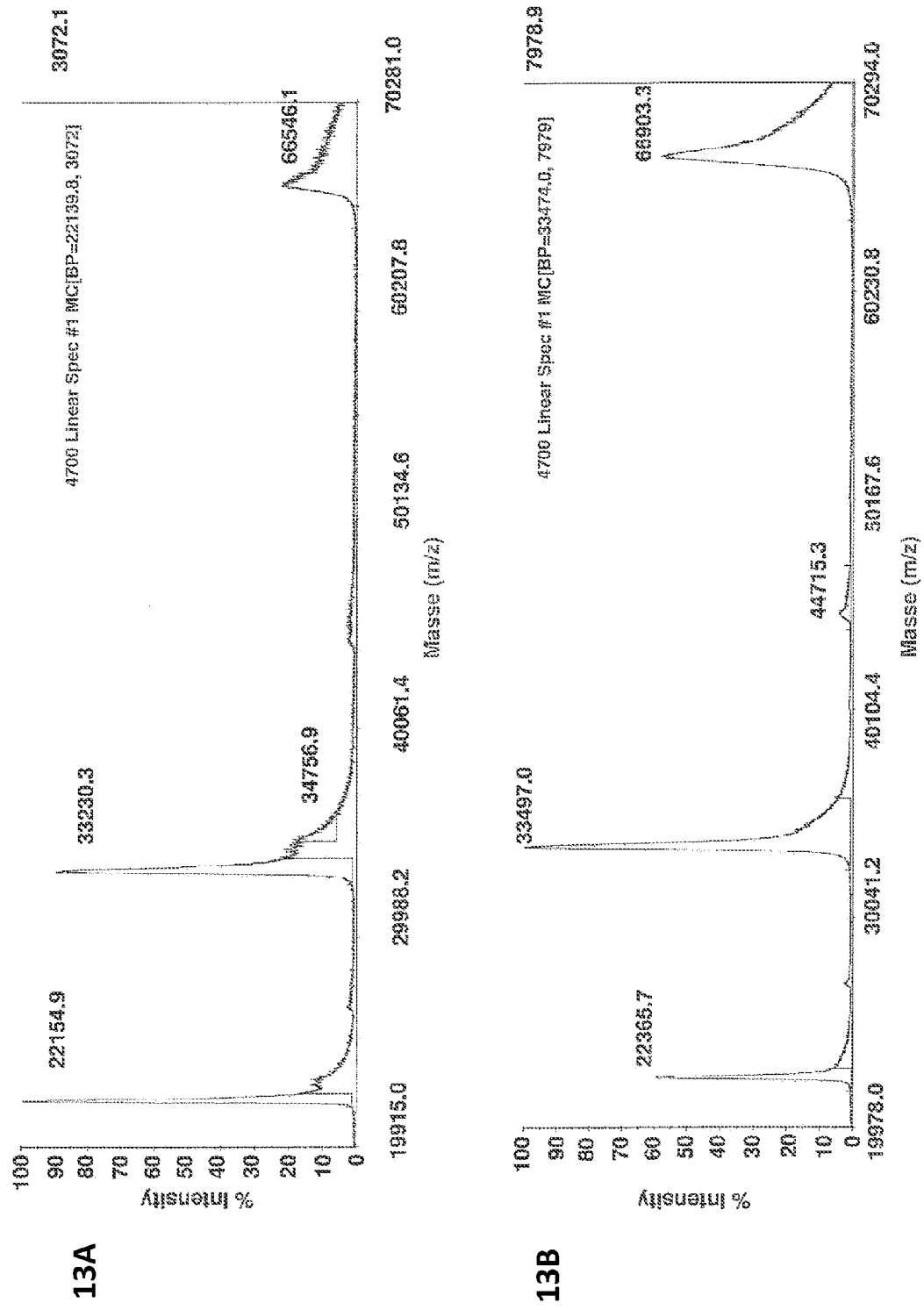
FIGS. 13A-B

FIGS. 16A-D
16A
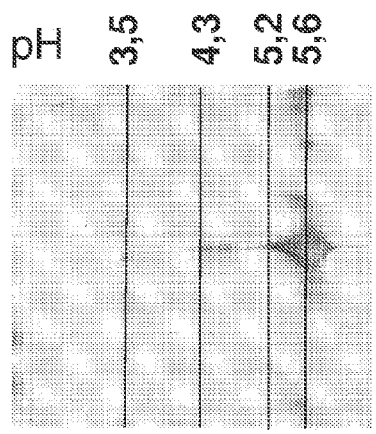
16B
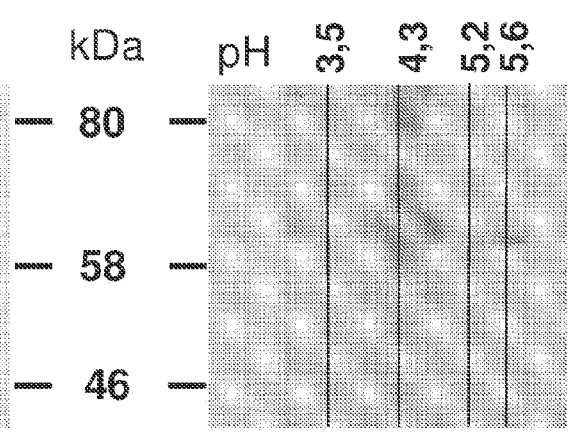
16C
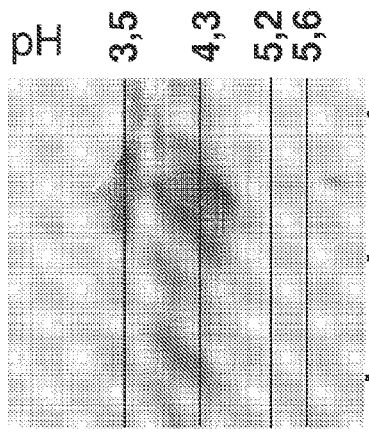
16D
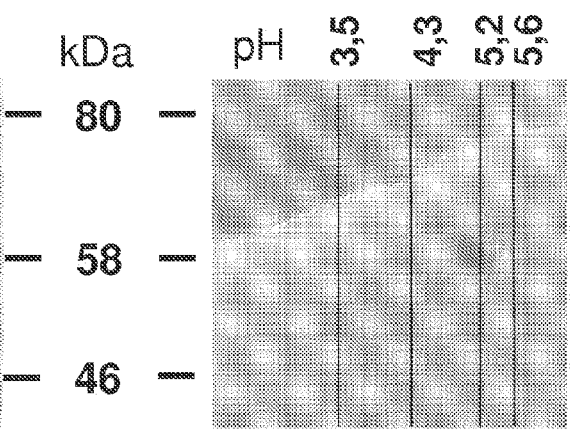

FIGS. 21A-B
21A
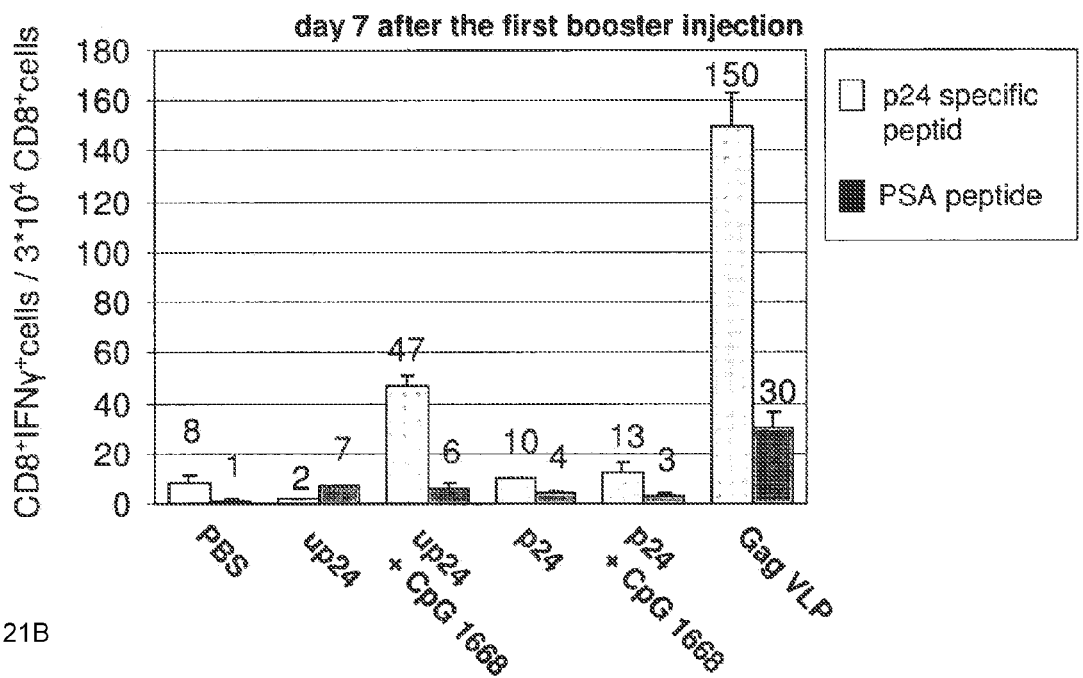
21B
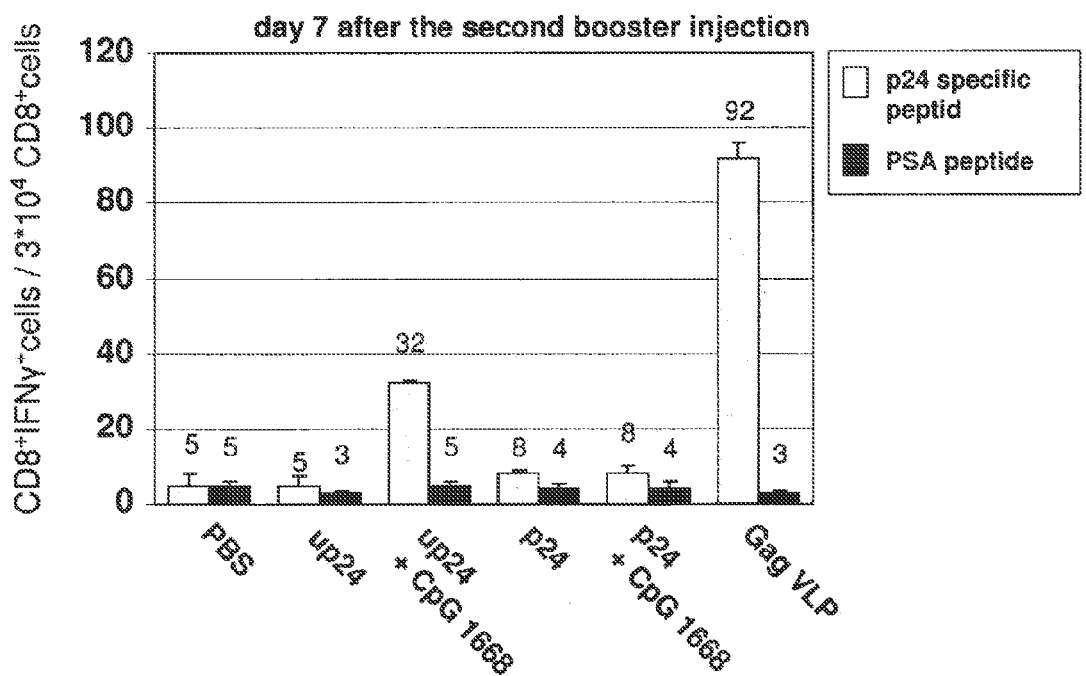

FIGS. 23A-B
23A
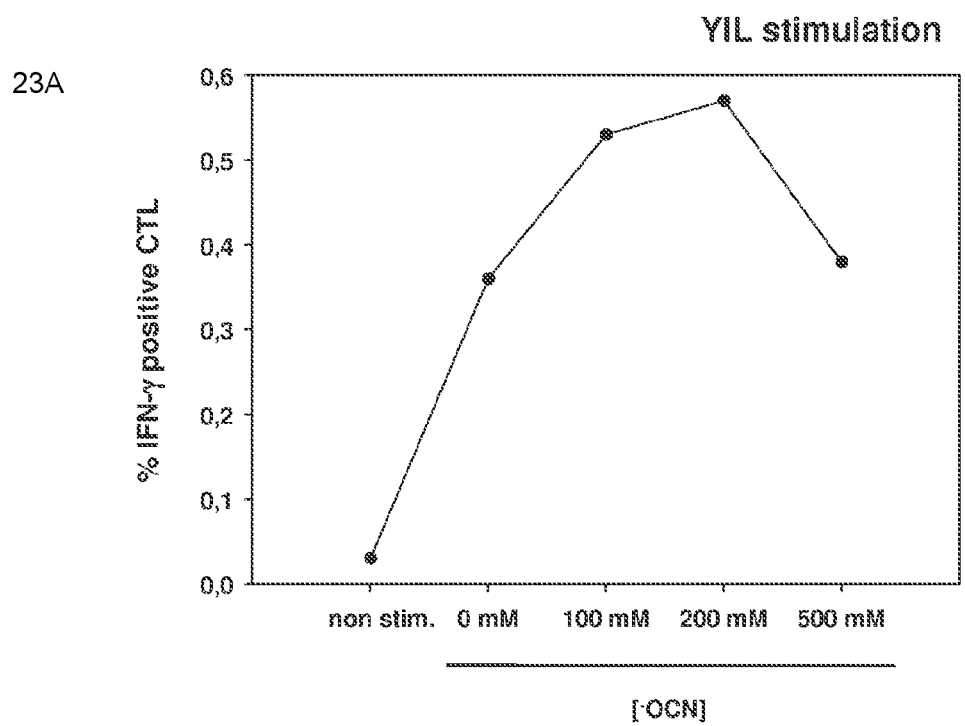
23B
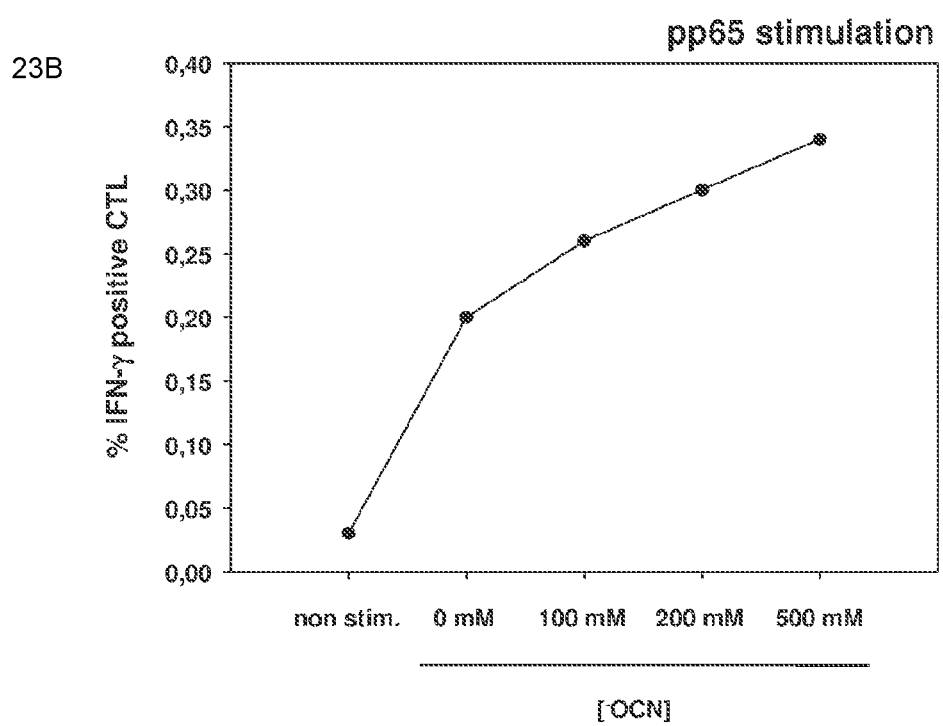

METHOD FOR THE DETECTION OF POLYPEPTIDE SPECIFIC IMMUNE CELLS

This application is a divisional of U.S. application Ser. No. 13/263,641, which was filed Oct. 7, 2011, as a national phase application under 35 U.S.C. §371 of International Application No. PCT/EP2010/054711 filed Apr. 9, 2010, which claims priority to European Application No. 09 157 777.5 filed on Apr. 9, 2009. The entire text of each of the above-referenced disclosures is specifically incorporated herein by reference without disclaimer.

The present invention relates to a method for polypeptide transfer into cells. The present invention further relates to the detection of polypeptide-specific immune cells and the priming, expansion and reactivation of polypeptide-specific T cells. Moreover the present invention relates to polypeptides of the methods of the present invention in combination with urea and their use for research, diagnosis or treatment and prevention of diseases in animals and humans.

The acquired branch of the immune system consists of a humoral (immune globulins) and a cellular immune defence.

Cellular and microbial polypeptides are processed from antigen-presenting cells (APC) by specific cleavage and fragments (epitopes) thereof are presented together with MHC molecules of class I and/or II on the cell surface. By means of their T-cell receptor, T cells specifically recognise epitopes presented in the complex with the MHC proteins and start an immune reaction.

T cells can be subdivided into different effector populations using specific surface proteins. $CD4^+$ T cells (T helper cells) recognize peptides, which are presented to them on the surface of APC together with MHC class II proteins and play a crucial role in the orchestration and polarisation of the immune defence. T helper cells can be subclassified into T helper 1 (Th-1), T helper 2 (Th-2) and T helper 17 (Th-17) cells. Th-1 cells are characterized by the production of the cytokines IFN-$\gamma$ and TNF-$\alpha$ and the expression of the transcription factor T-bet. Th-1 cells activate cellular immune responses by enhancing the killing efficacy of the macrophages and stimulating the proliferation of cytotoxic $CD8^+$ T cells (cytotoxic T cells (CTL) or $CD4^-CD8^+$ T cells). Th-2 cells are characterized by the secretion of IL-4, IL-5, IL-6, IL-10 and IL-13 and the production of the transcription factor GATA-3 and support the production of antibodies as well as the antibody class switch (humoral branch of the immune response). Th-17 cells are characterized by the production of IL-17 and are thought to play a key role in autoimmune diseases.

Besides Th-1, Th-2 and Th-17 cells, the population of $CD4^+$ T cells includes approximately 10% regulatory T cells playing an essential role in the dampening of immune responses, in the prevention of autoimmune diseases and in oral tolerance. Regulatory T cells can be subdivided in CD4-, CD25- and CTLA4-positive natural regulatory T cells (Treg) as well as Th3 and Tr1 cells, which are characterized by the production of TGF-$\beta$ (Th3 cells) or IL-10 (Tr1 cells).

The importance of $CD8^+$ T cells lies in the recognition and destruction of degenerated, neoplastic and malignant cells as well as tissue and cells, which are infected by microorganisms or parasites. T cells are thus an important protection mechanism of the acquired immune system for the prevention and control of microbial, especially virus-induced diseases, and for the recognition and destruction of degenerated and neoplastic cells. In addition to the above mentioned T cell populations, other subpopulations of circulating T cells have been described, which have a double positive $CD4^+CD8^+$ phenotype (e.g. $CD4^+CD8^{dim}$, $CD4dimCD8^{bright}$ and $CD4^{hi}CD8^{hi}$ T cells).

$CD4^+CD8^{dim}$ T cells express $CD8\alpha\alpha$ homodimers and can be detected with a lower frequency (less than 2% of the total population of $CD3^+$ T cells) in the blood. A transient or persistent expansion of $CD4^+CD8^{dim}$ T cells was observed both in healthy persons and also in patients with various diseases, including infections with different viruses, for example, the human immune deficiency virus type 1 (HIV-1) and the human cytomegalovirus (CMV) as well as patients with various autoimmune diseases. $CD4^{dim}CD8^{bright}$ T cells are an activated phenotype of $CD8^+$ T cells, as determined by elevated levels of a number of activation and functional markers (CD95, CD25, CD38, CD69, CD28 and $CD45RA^+$ $CD45RA0^+$) in comparison to their $CD4^-CD8^+$ counterparts. $CD4^{hi}CD8^{hi}$ T cells express high levels of CD4 molecules and $CD8\alpha\beta$ chains and are increased in autoimmune conditions.

Professional APC such as dendritic cells, monocytes, macrophages but also non-professional APC such as B cells, neutrophiles and fibroblasts play a central role both in the triggering of a T cell response to exogenous and endogenous immunogens and in the induction of a T cell tolerance to endogenous tissue. The activation and proliferation of T cells takes place by the simultaneous triggering of two signals. The first signal is guided into the T cell by the T cell receptor which recognises the epitope in association with MHC on the surface of the APC. The second, co-stimulatory signal is mediated by the specific interaction of co-stimulatory molecules such as B7.1 (CD80) or B7.2 (CD86) on the APC with the relevant receptor (such as CD28) on the surface of the T cell. In the absence of the co-stimulatory signal, the epitope-specific T cell becomes anergic. Anergy describes a state in which the T cells cannot multiply and cannot respond to an antigen.

The condition of a polypeptide decisively determines the efficiency and route of the epitope processing and presentation by an APC. In addition, the degree of activation of an APC and thus the profile of the induced immune response is adversely influenced by the form of administration of a polypeptide. Thus, the concentration and biochemical properties of a polypeptide as well as the presence or absence of immunomodulatory substances (especially bacterial components such as nucleic acids (e.g. CpG-positive DNA), lipopolysaccharides (LPS) and polypeptides (e.g. flagellin) as well as cytokines (e.g. IL-4, IL-5, IL-10, IL-12, IFN-$\gamma$, IL-18, IL-23) are determining factors as to whether the cellular (T helper-1 (Th-1)-type mediated immunity) or humoral branch (T helper-2 (Th-2)-type mediated immune response) of the immune system is activated or whether the immune response proceeds tolerogenic.

Hitherto, only few methods for the translocation of exogenous polypeptides into mammalian cells have been described. Furthermore, only few methods for the translocation of exogenous polypeptides into the MHC class-I processing pathway of APC have been described. Hitherto, for example, mechanical methods of microinjection, electroporation and lipofection had been used with varying success for transferring protein into cells.

Other methods for polypeptide transfer into cells are based on using protein transduction domains (PTD). These arginine-rich amino acid sequences comprising 10 to 35 amino acids originate for example from the HIV Tat protein, the Herpes Simplex Virus (HSV) VP22 protein or the Drosophila Antennapedia homeoprotein (Antp). In addition, synthetic PTD sequences were determined by means of phage libraries. The membrane prevalence and translocation of polypeptides can be increased considerably by their coupling with PTD.

Other methods described for protein transfer into cells are based on using various cationic lipid formulations or the incorporation of polypeptides in ISCOM® particles (immunostimulatory complexes containing saponin, cholesterol and phospholipid; CSL Limited, Victoria, Australia). All these methods are too work- or cost-intensive for routine use. In addition, many of the particular transfer systems possess cytotoxic (for example liposomes) or immune-modulatory properties (ISCOM® particles; immunostimulatory complexes containing saponin, cholesterol and phospholipid) which can subsequently adversely influence the natural properties of the treated cells.

Bearing in mind the importance of the cellular immune response, especially cytotoxic T cells (CTL) for controlling microbial infections and tumours, many new strategies for the in vivo priming of CTL in addition to T helper cells are currently being tested. These include the use of peptides, polypeptides, proteins, virus-like particles, living attenuated bacteria and viruses, recombinant living vaccines (based on various recombinant bacteria and viruses) and DNA vaccines.

Furthermore, ex vivo treated autologous APC which present specific peptides in the context with MHC proteins of classes I and II are a suitable reagent for the induction of polypeptide-specific immune responses, especially in therapeutic treatments. In earlier studies, APC pulsed with tumour extracts, cell lysates, expression plasmids and messenger RNA have proved suitable for simultaneously inducing $CD4^+$ and $CD8^+$ T cell responses (Herr et al. (2000), Blood, 96:1857). Moreover, it is described in EP 0 421 949 B1 that chemical modified allergens pretreated with alkaline metal cyanate can be used for the induction of specific antibodies of the IgG class.

At the present time, various methods are available for stimulating various populations of immune cells which are suitable to different extents for detecting specific populations of antigen-specific immune cells.

Direct loading of membrane-bound MHC proteins with peptides of defined length (optimally 8-12 amino acids for loading MHC class I proteins and optimally 16 to 22 amino acids for loading MHC class II proteins) is a method frequently used for stimulating defined populations of immune cells, especially $CD8^+$ T cells and $CD4^+$ T cells. In addition, 14- to 16-mer peptides can be used for the simultaneous activation of $CD4^+$ and $CD8^+$ T cells. However, important restrictions on the use of this stimulation method for the measurement of protein-specific T cells lie in the fact that specific recognition of T cell epitopes is subjected to an MHC restriction; that is, persons who express different MHC proteins recognise different epitopes within a polypeptide which makes the analysis of polypeptide-specific T cells in blood donors with variable MHC patterns considerably more difficult.

In addition peptides of different size (8- to 12- and 18- to 22-mers) are preferentially presented on MHC class I or II proteins. Thus, only T cells which are directed against known epitopes in the context with defined MHC proteins can be specifically registered using this method.

Alternatively, peptide pools (e.g. 14 to 16-mer peptides overlapping in 13 amino acids), spanning the complete protein can be used for the simultaneous detection of protein-specific T cells. However, the production of pools of overlapping peptides covering complete proteins is expensive and costly.

In addition, the application of many peptides including known T cell epitopes is restricted by its low capacity to activate T cells. Herein, the efficiency of T cell activation by MHC/peptide complexes is dependent on (i) the affinity of the peptide to the MHC molecule, (ii) the stability of peptide MHC complexes and (iii) by the affinity of T cell receptor to MHC/peptide complexes.

Yet, only one technology has been described to increase the efficiency of epitopes to stimulate T cells. The group of Peterson and coworkers reported that phosphorylated, HLA A2-restricted CTL epitopes reveal an altered capacity to stimulated CTL, when compared to their non phosphorylated counterparts (Petersen et al. (2009), PNAS 106: 2776-2781).

In contrast, soluble polypeptides and proteins are suitable for detecting polypeptide-specific $CD4^+$ T cells regardless of the MHC restriction of the donor and the detailed knowledge of the T cell epitope localised in a polypeptide. Soluble polypeptides are almost exclusively taken up and recovered via the MHC class II processing and presentation route in APC so that this method is almost exclusively suitable for detecting $CD4^+$ T cells.

Furthermore, various methods for denaturing polypeptides have also been described which make it possible to supply these polypeptides to the MHC class I and MHC class II processing and presentation route. These methods include, for example, treatment of polypeptides with heat or sodium dodecyl sulphate (SDS). These methods proved to be suitable for achieving an epitope presentation on MHC class I and II molecules in murine APC (Schirmbeck et al. (1994), Eur. J. Immunol., 24:2068); (Schirmbeck et al. (1995), Vaccine, 13:857). In these studies it was shown that proteins denatured in various ways are taken up into the APC by means of various mechanisms and differ in terms of their efficiency to induce polypeptide loading of MHC class I molecules. Thus, compared with SDS-treated proteins, polypeptides treated using the heat inactivation method (1 hour at 60° C. or 15 min at 100° C.) only induced a slight stimulation of epitope presentation on MHC class I proteins in treated murine APCs. On the other hand, the SDS denaturing method proved to be little suited for use in human cell cultures because of the high toxicity. Another method for the pre-treatment of polypeptides is described in EP 1 487 497 B1, in which the polypeptides are pretreated with urea.

Another method for stimulating the MHC class I and II presentation of epitopes on APC is based on the incorporation of polypeptides in particular structures, for example, liposomes, particular carrier substances, virus-like particles or lipoprotein particles. The first studies confirmed the suitability of HIV-1 $Pr55^{gag}$ virus-like particles for the diagnosis of $CD4^+$ and $CD8^+$ T cells (Sester et al. (2000), AIDS, 14:2653-60). However, the production of particle-bound polypeptides is expensive and costly.

Another method for stimulating the MHC class I and II presentation of epitopes on APC is based on the incorporation of polynucleotides coding for the desired polypeptides using plasmids, non-viral or viral vectors. A disadvantage of using plasmids for diagnostic purposes is the low efficiency and cytotoxic effects of the nucleic acid transfer into APC using the hitherto available transfection methods, for example electroporation or lipofection. Viral or bacterial vectors frequently have significantly increased transfection rates of APCs compared to plasmids. However, these gene transfer systems are frequently not immunologically inert and modulate the capability of APC for epitope processing and presentation of polypeptides. In addition, the use of these nucleic-acid-based methods is limited by the expensive and costly production of gene ferries.

So far CD4$^+$ T cells have been detected by determining the cell proliferation or the messenger substances (cytokines) produced by T cells after a specific stimulation. The cell proliferation is usually detected using a conventional tritiated thymidine ($^3$H-TdR) incorporation assay or nonradiolabelling proliferation assays such as 5-bromo-2-deoxyuridine (BrdU) ELISA, tetrazolium microplate assay and acid phosphatase assay.

The cytokine production from CD4$^+$ T cells after a specific stimulation with polypeptides can be determined by means of a cytokine ELISA, an ELISPOT assay or by means of FACS technology by determining intracellular cytokines (e.g. intracellular cytokine staining) or secreted cytokines (e.g. FACS secretion assay).

CD8$^+$ T cells have conventionally been detected by determining their specific cytotoxic activity or the messenger substances (cytokines) produced by CD8$^+$ T cells after a specific stimulation, especially of interferon-$\gamma$ (IFN-$\gamma$). The cytotoxicity is usually detected by means of a classical chromium release test or adequate non-radioactive method in which the release of enzymes or ATP from target cells as a result of a specific lysis by the effector cell with cytotoxic properties is measured. Alternatively, cytotoxic activity of CD8$^+$ T cells can be measured by determining transient surface expression of CD107a,b (LAMP 1,2 proteins).

The cytokine production from CD8$^+$ T cells after an epitope-specific stimulation can be determined by means of a cytokine ELISA, an ELISPOT assay or by using FACS technology by determining intracellular cytokines or secreted cytokines (FACS secretion assay). IFN-$\gamma$, TNF and IL-2 are usually used as marker cytokines for the presence of polypeptide-specific CD8$^+$ T cells. So far, autologous APC which present CD8$^+$ T cells epitopes in conjunction with MHC proteins of class I on their surfaces, have been used, for example, to stimulate epitope- or polypeptide-specific CD8$^+$ T cells. The induction of an MHC class I mediated epitope presentation on APC has so far been mediated by incubating this with epitope-carrying peptides of suitable length (8 to 16 amino acids), by incubating with lipopolypeptides, particular polypeptides or polypeptides packed in particular structures, lysates of polypeptide-producing cells as well as recombinant and live attenuated micro-organisms, especially viruses or bacteria.

The tetramer (Coulter), pentamer (Proimmune) and streptamer technology (IBA, Gottingen) are methods for detecting epitope-specific CD8$^+$ T cells and CD4$^+$ T cells. However, limitations of these methods for widespread use in T cell diagnostics are based on the very high costs for the manufacture of these reagents. In addition, tetramers, pentamers and streptamers has so far only been available for a limited repertoire of MHC types, especially for frequent MHC class I proteins, for example, HLA A2. In addition, this technique only allows the detection of defined epitope-specific T cells. T cell reactivities against multiple epitopes can only be determined using this method with a substantial expenditure of time and money.

It is thus the object of the present invention to provide a new method for the polypeptide transfer into cells.

This object is solved by the subject matter defined in the claims.

The following figures are used to explain the invention.

FIG. 1 shows the reaction mechanism for the carbamoylation of primary amines. (A) Urea is in equilibrium with ammonium and cyanate. Heat and/or time drive the reaction towards the breakdown of urea, causing a buildup of cyanic acid. (B) At neutral to basic pH, the cyanic acid undergoes nucleophilic attack by primary amines forming the carbamoylated amine as demonstrated by the carbamoylation of proteins, wherein especially the amino terminus but also lysines in general and other amino acids of the protein are carbamoylated (Angel et al. (2007) *Rapid Commun. Mass Spectrom.* 21:1623).

Figure 2:
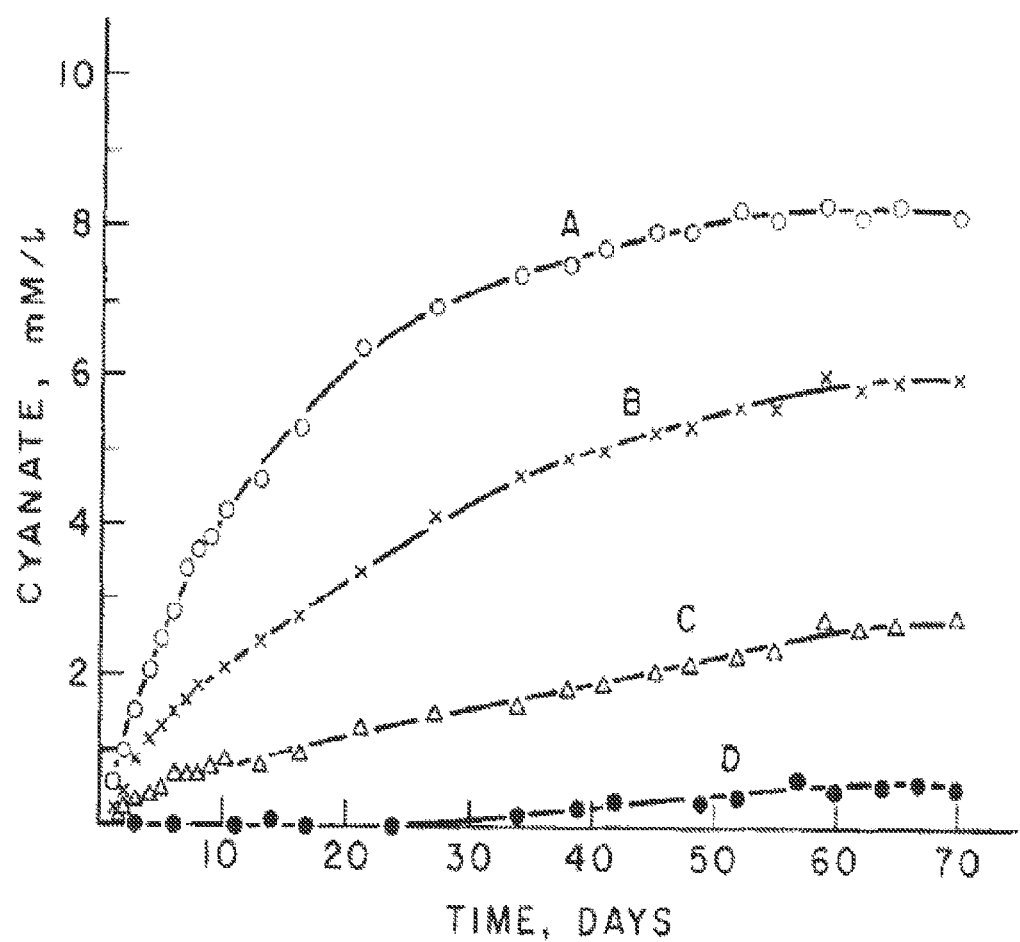
FIG. 2 shows cyanate accumulation in urea solutions held at low temperature. Curves A, B, and C—6.66, 3.33, and 1.11 M urea, respectively, held at 25° C., Curve D—6,66 M urea held at 5° C. (Marier et al. (1964) *Analytical Biochemistry* 7:304).
Figure 3:
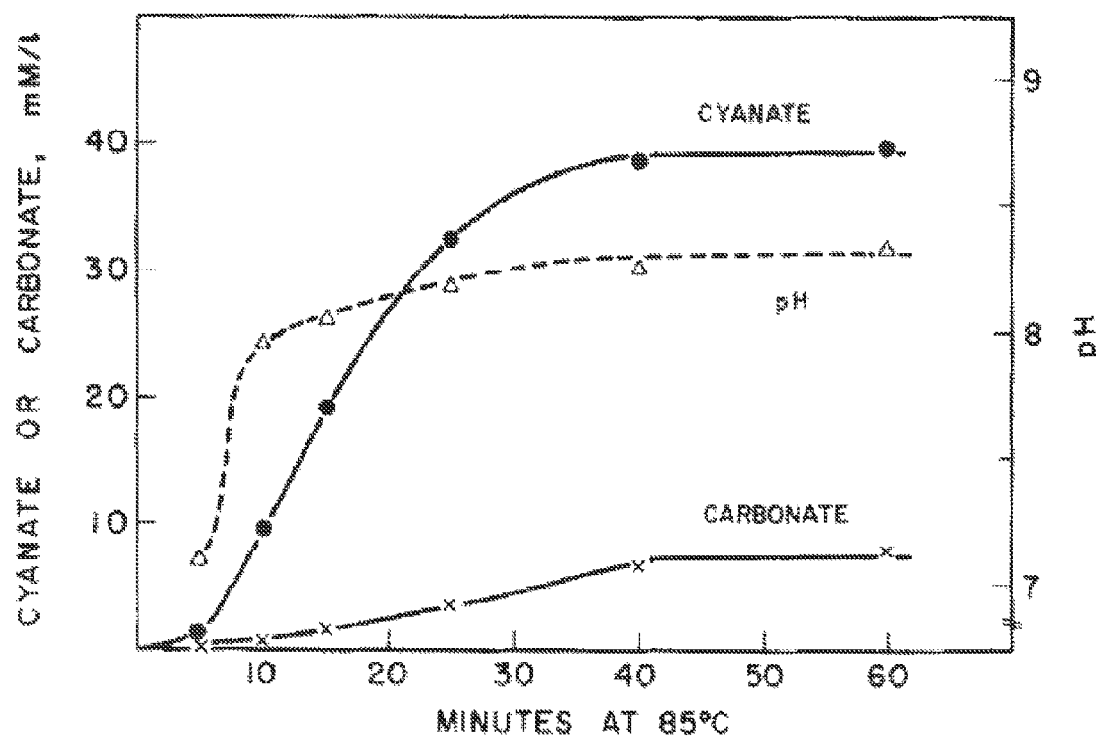
FIG. 3 shows cyanate accumulation and related changes in 6.66 M urea held at 85° C. (Marier et al. (1964) *Analytical Biochemistry* 7:304).
Figure 4:
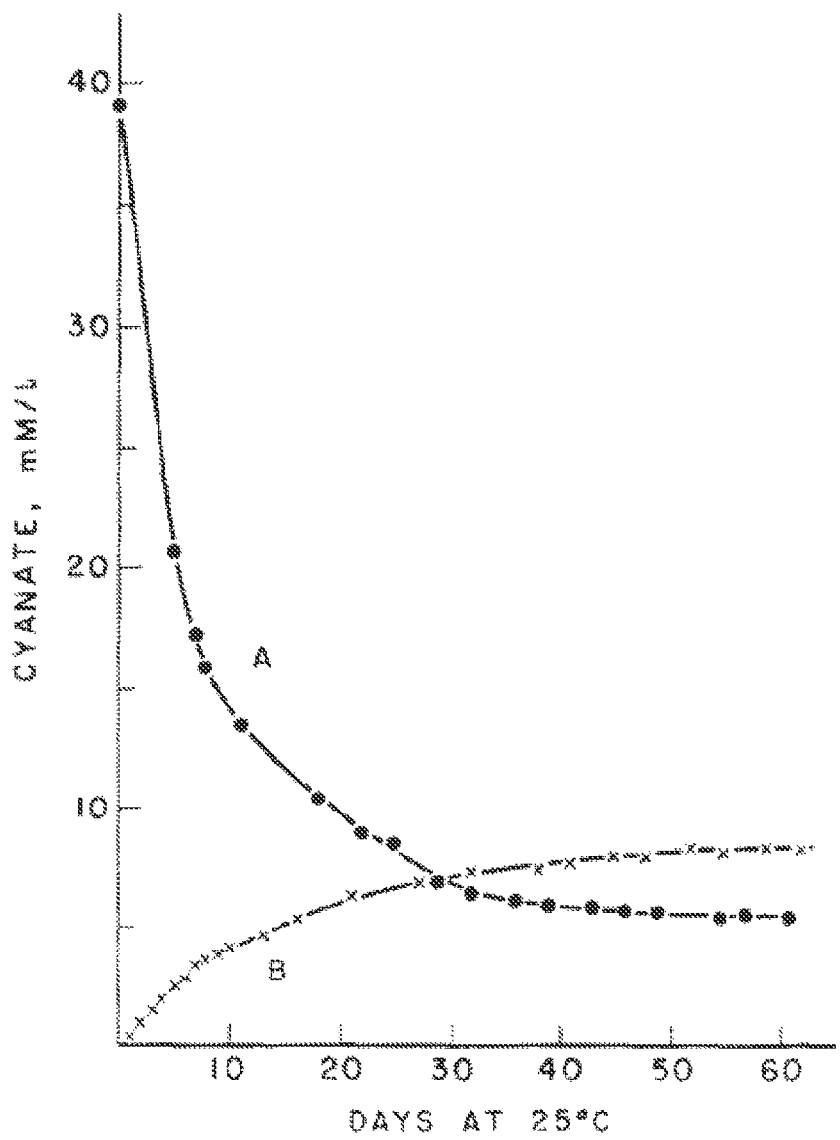

FIG. 4 shows changes in cyanate concentration in 6.66 M urea held at 25° C. Curve A reequilibration of a heated solution (i.e., 85° C., 50 minutes). Curve B—direct equilibration (Marier et al. (1964) Analytical Biochemistry 7:304).

Figure 5:
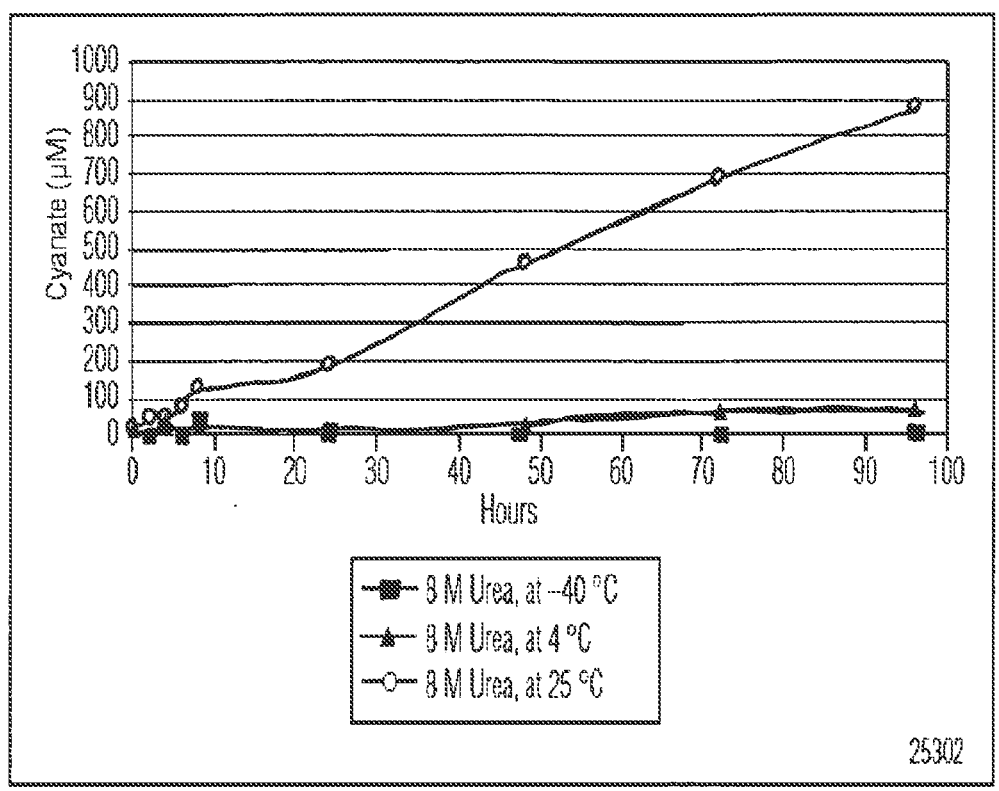

FIG. 5 shows the changes in cyanate concentration in 8 M urea held at −40° C., at 4° C. and at 25° C. (Christison et al, "Direct Determination of Cyanate in a Urea Solution and a Urea Containing Protein Buffer Using a Reagent-Free Ion Chromatography System", Dionex (www.dionex.com))

Figure 6:
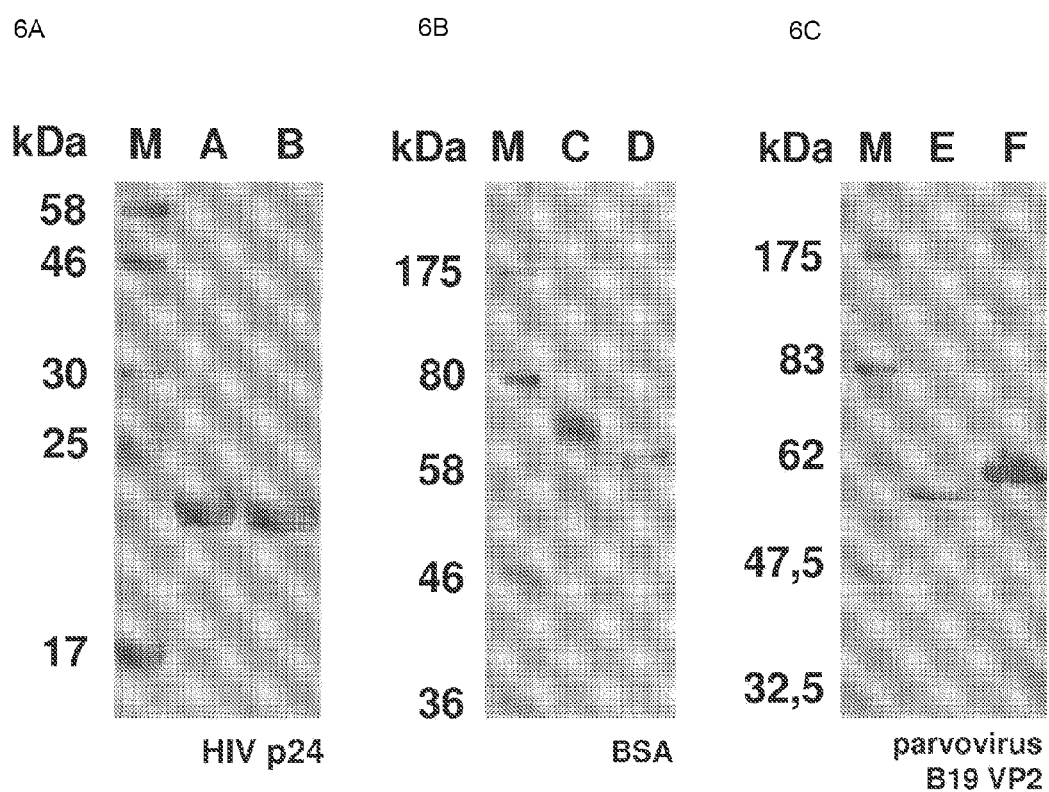

FIGS. 6A-C show that heating of polypeptides in a 2 M urea solution (final concentration) results in an altered migration behavior of proteins in polyacrylamide gels. (6A) 0.84 mg/ml HIV capsid protein p24 (dissolved in 150 mM NaCl, 50 mM NaP, pH 7.6), (6B) 1 mg/ml bovine serum albumine (BSA) or (6C) 0.64 mg/ml parvovirus B19 VP2 particles (dissolved in 38% (w/v) CsCl) were mixed 1:1:1 (vol/vol/vol) with (columns B,D,E) H$_2$O and 30 mM Tris pH 3.9 or (columns A,C,F) 6 M urea-solution and 30 mM Tris pH 3.9 and then incubated for 60 min at 96° C. in a thermomixer. Then, proteins were separated by (6A) 12.5% or (6B,6C) 10% SDS-polyacrylamide gel electrophoresis (PAGE) and proteins were visualized by staining with coomassie brilliant blue. M: molecular weight markers (6A,6B): Colour Plus prestained protein marker, broad range NEB P7703; (6C): Prestained protein marker, broad range NEB P7703. Sizes are indicated in kilo daltons (kDa).

Figure 7:
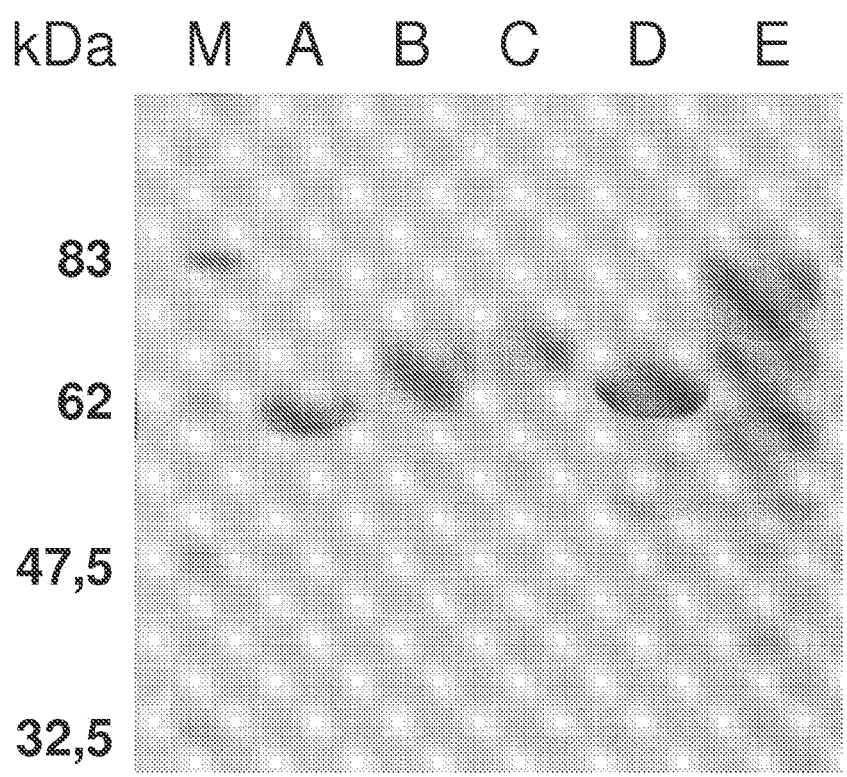

FIG. 7 shows that the treatment with urea following different carbamoylation protocols results in modified BSA proteins revealing increased molecular weights, as shown by an altered migration in polyacrylamide gels. 1 mg/ml BSA was mixed 1:1:1 (vol/vol/vol) with (A) H$_2$O/HCl (pH 3.6) and 30 mM Tris pH 3.6 or (B,C) 6 M urea-solution and 30 mM Tris pH 3.6 and incubated (A) for 0 min at 96° C. or (B) 30 min at 96° C. or (C) 60 min at 96° C. (D) BSA was treated following a protein carbamoylation protocol described by Angel and coworkers (Angel et al. (2007) *Rapid Commun. Mass Spectrom.* 21:1623). 10 nmol BSA was dissolved in 100 µl 8 M urea/200 mM Tris-HCl, pH 7.4. This solution was reduced with 20 mM dithiothreitol (DTT) for 2 hours at 50° C., followed by carbamidomethylation with 45 mM iodoacetamide (IDA) at room temperature for 1 h. The solution of denatured, reduced and alkylated proteins was diluted 1:8 with 50 mM ammonium bicarbonate to adjust the concentration of urea to 1 M and incubated overnight at 37° C. (E) BSA was treated as described in (D). Then, the solution was dried under vacuum at 37° C. and dissolved in 300 µl 8 M urea/200 mM Tris-HCl, pH 8.5. Then the sample was vortexed until complete solubilization and then incubated for 4 hours at 80° C., with periodic vortexing (according to Angel et al. (2007) *Rapid Commun. Mass Spectrom.* 21:1623). Then, proteins were separated by 10% SDS-polyacrylamide gel electrophoresis (PAGE) and visualized by staining with Coomassie brilliant blue. M: Prestained protein marker, Broad range NEB P7702. Sizes are indicated in kilo daltons (kDa).

FIGS. 8A-D show that treatment of BSA with urea following different carbamoylation protocols results in modified BSA proteins revealing an altered $pK_i$ value, as shown by two-dimension electrophoresis. 1 mg/ml BSA was mixed 1:1:1 (vol/vol/vol) with (8A) $H_2O$/HCl (pH 3.6) and 30 mM Tris pH 3.6 or (8B,8C) with 6 M urea-solution and 30 mM Tris pH 3.6 and incubated for (8A) 0 min (8B) 30 min or (8C) 60 min at 96° C. (8D) BSA was treated following a protein carbamoylation protocol described by Angel and coworkers (Angel et al. (2007) *Rapid Commun. Mass Spectrom.* 21:1623). 10 nmol BSA was dissolved in 100 μl 8 M urea/200 mM Tris-HCl, pH 7.4. This solution was reduced with 20 mM dithiothreitol (DTT) for 2 hours at 50° C., followed by carbamidomethylation with 45 mM iodoacetamide (IDA) at room temperature for 1 h. The solution of denatured, reduced and alkylated proteins was diluted 1:8 with 50 mM ammonium bicarbonate to adjust the concentration of urea to 1 M and incubated overnight at 37° C. Then, proteins were separated by isoelectric focusing on IEF strips (Immobiline™ DryStrip pH 3-10, 11 cm, GE Healthcare) at 26350 Vh followed by a 10% SDS-PAGE electrophoresis. Proteins were visualized by silver staining. M: Prestained protein marker, Broad range NEB P7702. Sizes of protein standards are indicated in kilo daltons (kDa).

Figure 9:
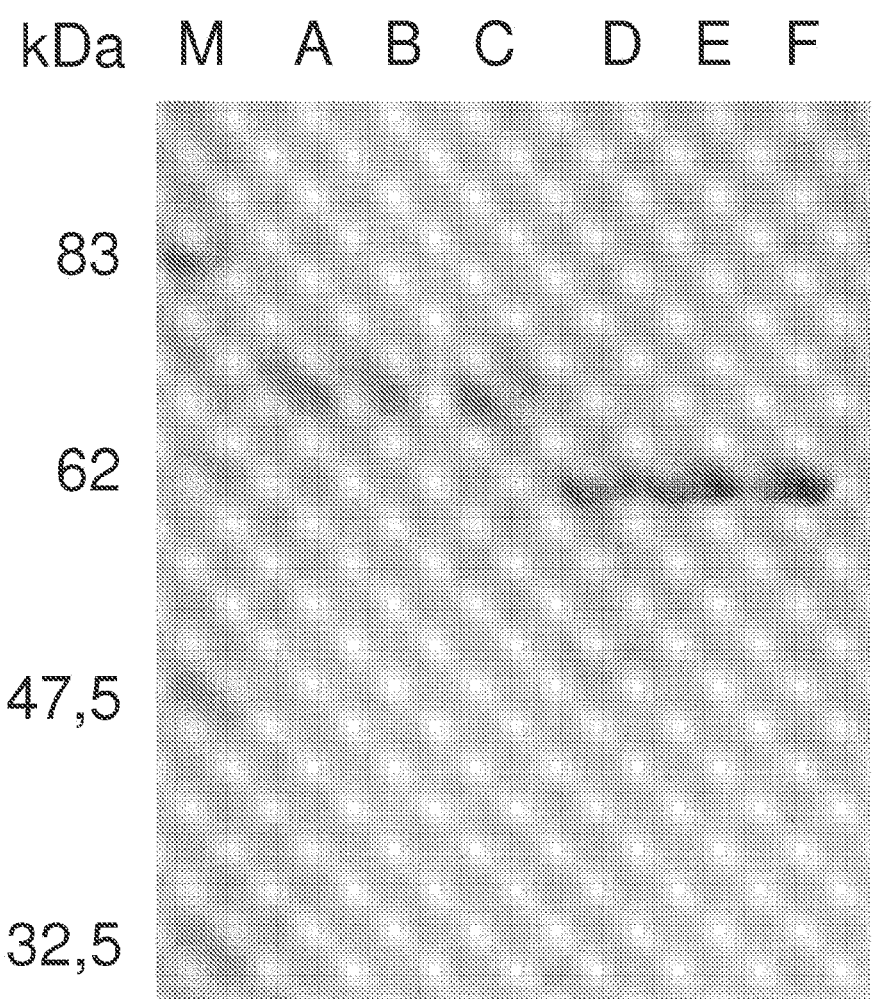

FIG. 9 shows that the modification of BSA by treatment with 2 M urea, 10 mM Tris (2 hours incubation at 96° C.) is not substantially influenced by the pH value, ranging from pH 3.9 to pH 8.7. 1 mg/ml BSA was mixed 1:1:1 (vol/vol/vol) with (A-C) 6 M urea and (A) 30 mM Tris pH 3.9 or (B) 30 mM Tris pH 6.8, or (C) 30 mM Tris pH 8.7 or with (D-F) $H_2O$ and (D) 30 mM Tris pH 3.9 or (E) 30 mM Tris pH 6.8 or (F) 30 mM Tris pH 8.7 and then incubated for 2 hours at 96° C. in a thermomixer (300 rpm). Then, proteins were separated by 10% SDS-PAGE and proteins were visualized by staining with Coomassie brilliant blue. M: Prestained protein marker, broad range NEB P7702. Sizes are indicated in kilo daltons (kDa).

FIGS. 10A-B show that the efficiency of urea-mediated modification of BSA is dependent on the incubation time. (10A) 1 mg/ml bovine serum albumine (BSA) was mixed 1:1:1 (vol/vol/vol) with 6 M urea and 30 mM Tris pH 3.9 and incubated at 96° C. for indicated incubation times (0 to 60 minutes). (10B) 1 mg/ml bovine serum albumine (BSA) was mixed 1:1:1 (vol/vol/vol) with 6 M urea and 30 mM Tris pH 3.9 and incubated at 96° C. for indicated incubation times (0-8 hours). Then, proteins were separated by 10% SDS-PAGE and proteins were visualized by staining with Coomassie brilliant blue. M: Prestained protein marker, Broad range NEB P7702. Sizes are indicated in kilo daltons (kDa).

Figure 11:
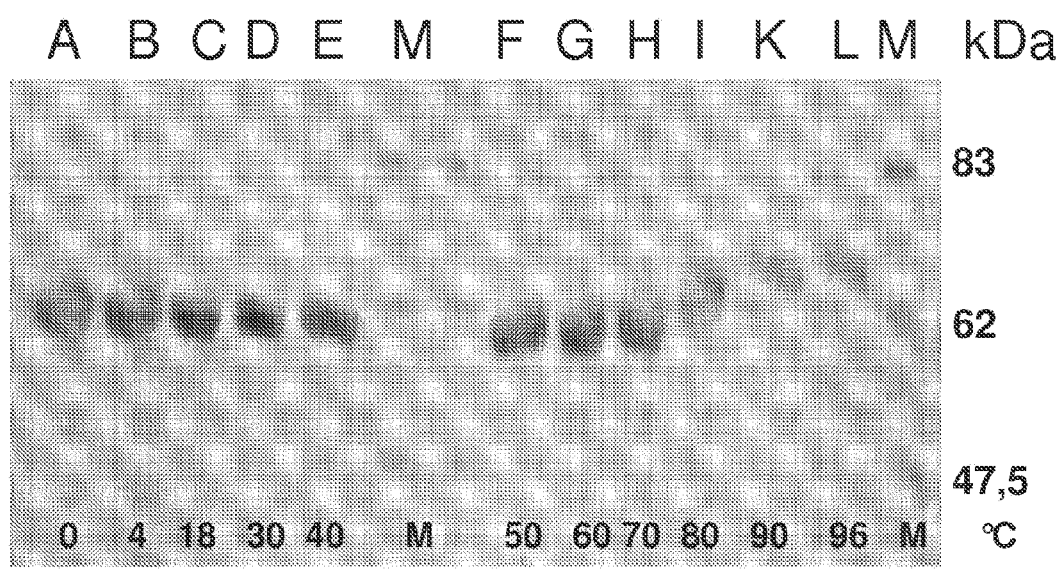

FIG. 11 shows that the efficiency of urea-mediated modification of BSA is dependent on the temperature. 1 mg/ml BSA in $H_2O$ was mixed 1:1:1 (vol/vol/vol) with 6 M urea and 30 mM Tris pH 3.9 (lane A-L) and incubated for 2 hours at indicated temperatures (0 to 96° C.). Then, proteins were separated by 10% SDS-PAGE and proteins were visualized by staining with Coomassie brilliant blue. M: Prestained protein marker, Broad range NEB P7702. Sizes are indicated in kilodaltons (kDa).

FIGS. 12A-B show that treatment of human cytomegalovirus (CMV) IE1 protein with deposed urea (7 to 14 days at room temperature, than heated for more than 1 hour at 96° C.) results in modified IE1 proteins revealing an altered $pK_i$ value, as shown by two-dimension electrophoresis. (12A) Either 100 μl IE1 protein (0.89 μg/ml in PBS) or (12B) TE1 in PBS mixed up 1:1 (vol/vol) with 8 M deposed urea (heated for more than 1 hour at 96° C., than kept for 7 to 14 days at room temperature) were incubated over night at 40° C. Then, proteins were separated by isoelectric focusing on IEF strips (pH 3-10, linear) at 38300 Vh followed by a 10% SDS-PAGE. Proteins were visualized by silver staining. M: Prestained protein marker, Broad range NEB P7703. Sizes are indicated in kilodaltons (kDa).

FIGS. 13A-B show a MALDI-TOF MS analysis of untreated BSA and BSA treated with deposed urea. Spectra were obtained from (13A) unmodified BSA; double-isotopic protonated mass 33230.3 and (13B) BSA after mixture (1:1; vol/vol) with deposed 8 M urea (7 to 14 days at room temperature, than heated for more than 1 hour at 96° C.); double-isotopic protonated mass 33497. Thus, under the described test conditions urea-treatment of BSA induced a mass shift of 226.7 Da.

Figure 14:

FIG. 14 shows that incubation temperature and time of pre-heating of urea are critical factors for the efficiency of urea-induced modification of BSA. 1 mg/ml BSA in $H_2O$ was mixed 1:1 (vol/vol) with either (A,C,E,G) freshly prepared 4 M urea solution or (B,D,F,H) 4 M urea, which was pretreated for 1 hour at 96° C. and then quickly cooled down. Then samples were incubated for (A,B) 0 hours, (C,D) 2 hours, (E,F) 4 hours or (G,H) 17 hours at 40° C. in a thermomixer (at 300 rpm). Then proteins were separated by 10% SDS-PAGE and proteins were visualized by staining with Coomassie brilliant blue. M: Colour Plus prestained protein marker, Broad range NEB P7703. Sizes are indicated in kilodaltons (kDa).

Figure 15:
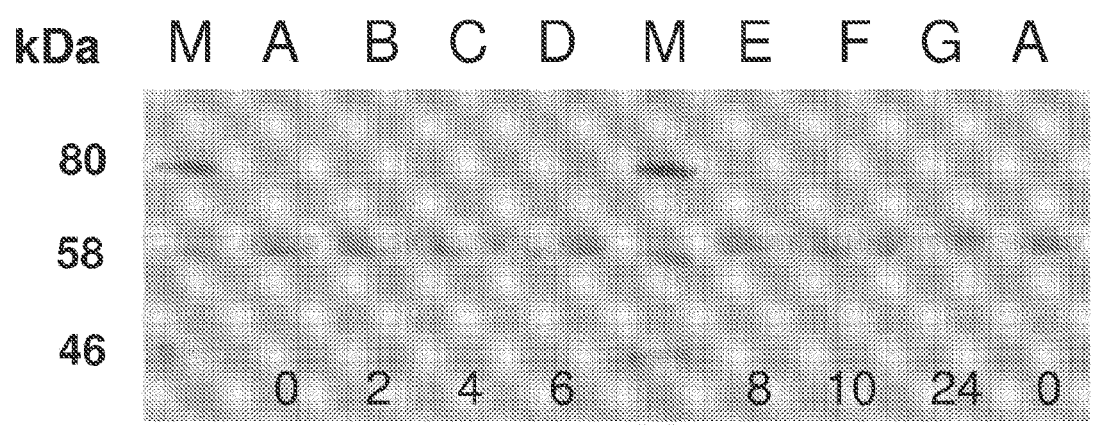

FIG. 15 shows that an incubation with deposed urea for 24 hours at 40° C. induces a mass shift of BSA. 1 mg/ml BSA in $H_2O$ was mixed 1:1 (vol/vol) with deposed 4 M urea (which was pretreated for 1 hour at 96° C. and then incubated for 8 days at room temperature) and incubated for indicated time points (0 to 24 hours) at 40° C. Then proteins were separated by 10% SDS-PAGE and proteins were visualized by staining with Coomassie brilliant blue. M: Colour Plus Prestained protein marker, Broad range NEB P7703. Sizes are indicated in kilodaltons (kDa).

FIGS. 16A-D show that treatment of BSA with urea following different carbamoylation protocols results in modified BSA proteins revealing an altered pKi value, as analysed by two-dimensional electrophoresis. 1 mg/ml BSA was mixed 1:1:1 (vol/vol/vol) with (16A) $H_2O$/HCl (pH 3.6) and 30 mM Tris pH 3.6 or (16B,16C) with 6 M urea-solution and 30 mM Tris pH 3.6 and (16A) incubated for 0 min, (16B) 30 min or (16C) 60 min at 96° C. (16D) Alternatively, 10 mM BSA was mixed 1:1 (vol/vol) with 4 M deposed urea (heated 1 hour at 96° C., then kept for 3 month at room temperature) and incubated 20 h at 40° C. Then, proteins were separated by isoelectric focusing on IEF strips at about (16A-D) 26350 Vh followed by a 10% SDS-PAGE electrophoresis. Proteins were visualized by silver staining. Sizes of protein standards are indicated in kilodaltons (kDa).

Figure 17:
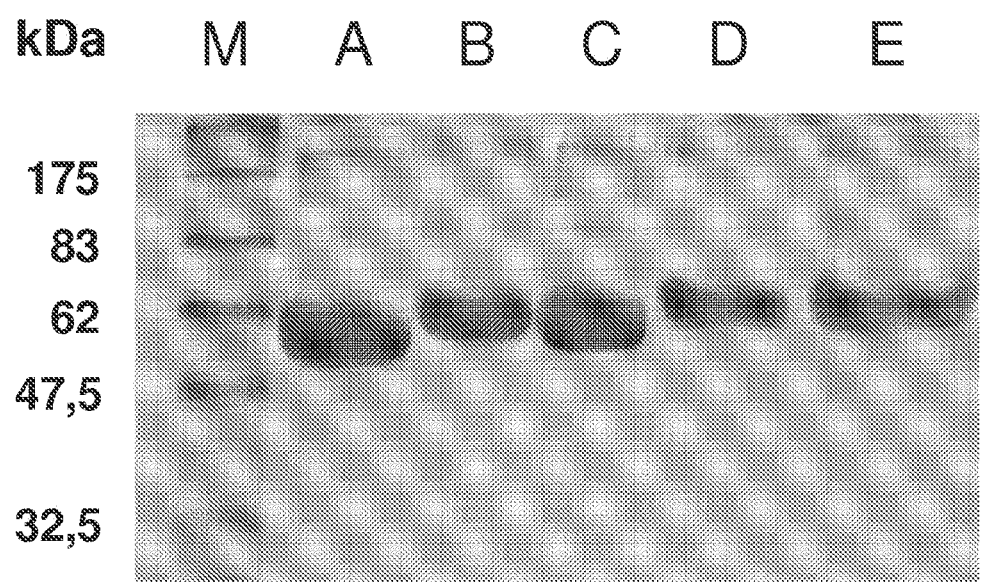

FIG. 17 shows chemical carbamoylation of BSA by potassium cyanate. BSA (1 mg/ml in water) was mixed 1:1 (vol/vol) for 1 hour at 40° C. in a thermomixer with potassium cyanate at final concentrations of (A) 0 mM, (B) 25 mM, (C) 100 mM, (D) 500 mM and (E) 1000 mM. The reaction products were separated by 10% SDS PAGE and visualized by staining with Coomassie brilliant blue. M: Prestained protein marker, Broad range NEB P7702. Sizes are indicated in kDa.

Figure 18:
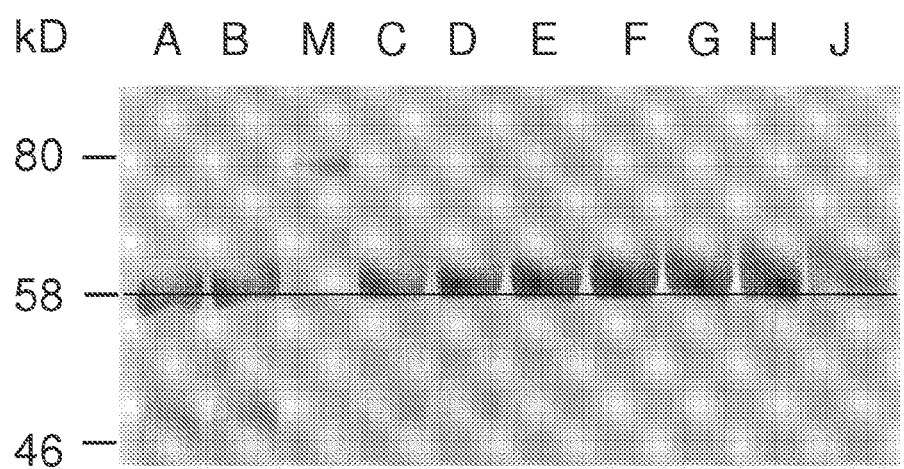

FIG. 18 shows chemical carbamoylation of BSA by potassium cyanate. BSA (1 mg/ml in water) was mixed (1:1 v/v) with increasing concentration of aqueous solutions of potassium cyanate (end-concentration KOCN: (A) 0 mM, (B) 1 mM, (C) 5 mM, (D) 10 mM, (E) 20 mM, (F) 50 mM, (G) 100 mM, (H) 200 mM, (J) 500 mM. Then, proteins were incubated for 19.5 h at 40° C. in a thermomixer and subsequently separated on a 10% SDS-gel. Proteins were visualized by staining with Coomassie brilliant blue. M: molecular weight marker (prestained protein marker, Broad range (NEB P7708)). Sizes of proteins are indicated in kilodaltons (kDa).

Figure 19:
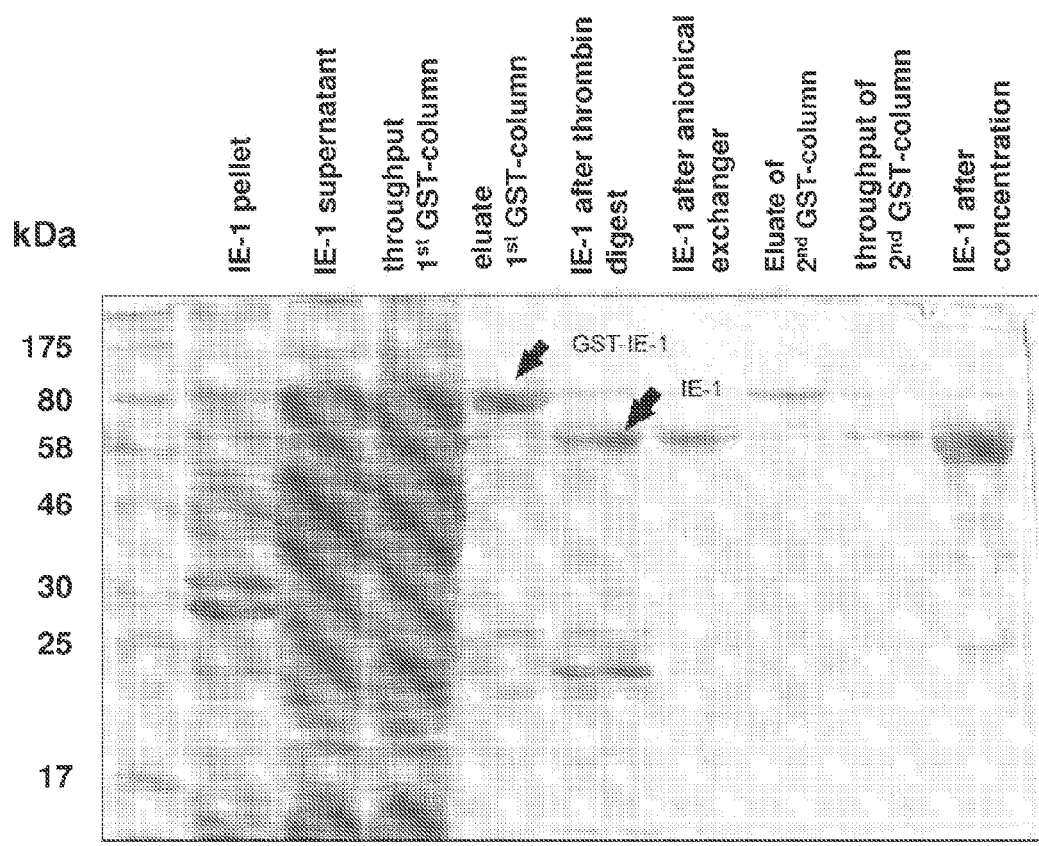

FIG. 19 shows the affinity purification of human cytomegalovirus IE1 proteins from lysates of pGEX-KG-IE1 transfected bacteria (M15[pREP4]). The samples of indicated purification steps were separated on a 12.5% SDS-PAGE and stained with coomassie brilliant blue. Marker: Prestained protein marker, Broad Range (Biolabs; NEB7703), sizes are indicated in kDa.

Figure 20:
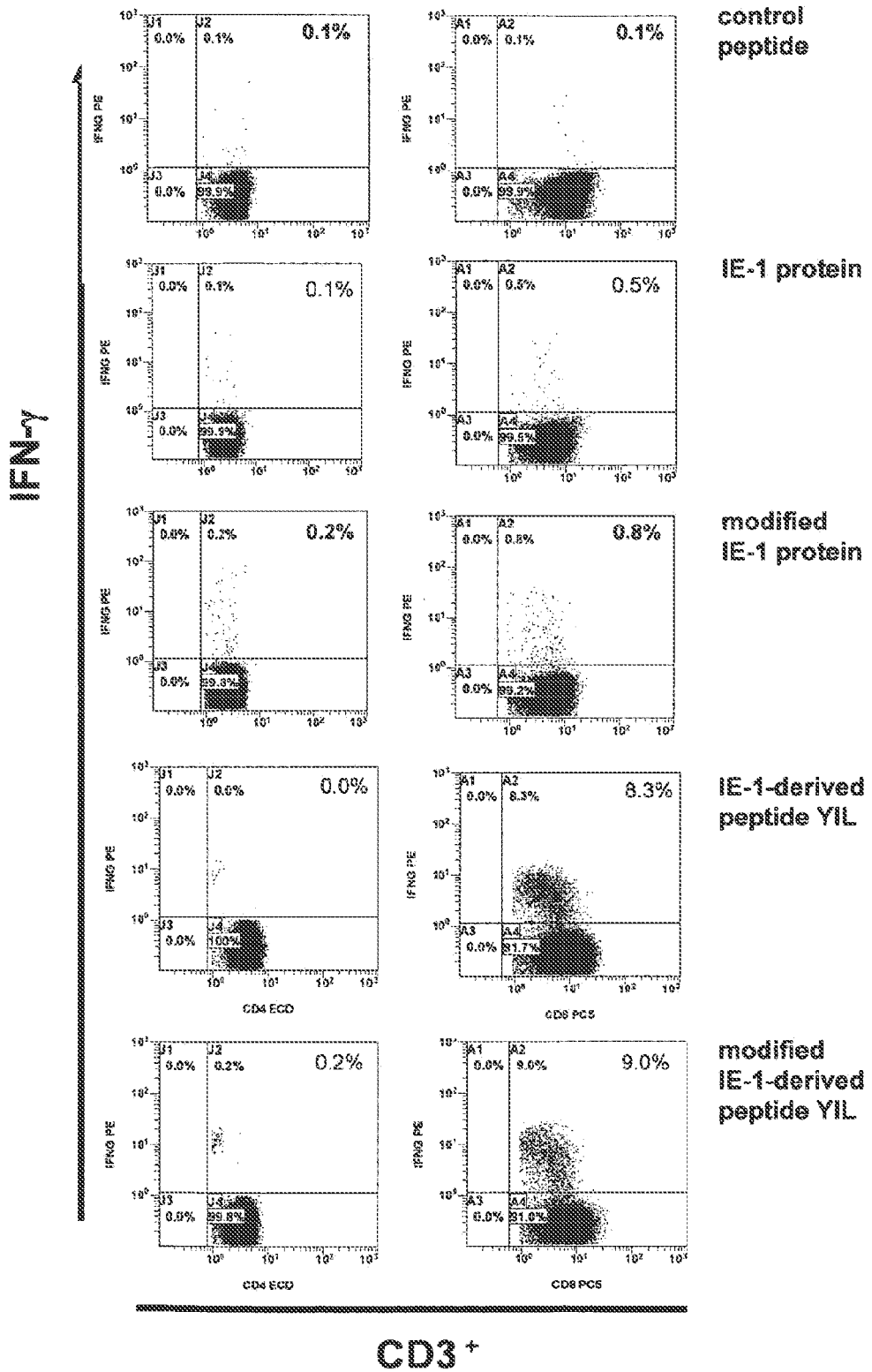

FIG. 20 shows the increased capacity of urea-modified polypeptides to specifically reactivate $CD4^+$ and/or $CD8^+$ T cells by the flow-cytometric analyses of heparinised whole blood of a CMV-positive HLA A2-positive individual after restimulation with synthetic peptides or recombinant CMV IE1 protein either in carbamoylated or not carbamoylated forms. In these experiments, purified IE1 protein (0.89 µg/ml in PBS) was mixed 1:1 (Vol/Vol) with 8 M deposed urea (preincubated over night at 96° C.) and incubated over night at 40° C. Peptides (10 µg/µl in 100% DMSO) were mixed 1:1 (Vol/Vol) with 8 M deposed urea (preincubated over night at 96° C.) and incubated over night at 40° C. Shown are $CD4^+$ Th cells and $CD8^+$ cytotoxic T cells and analyzed for IFN-γ secretion as determined by intracellular cytokine staining. Heparinized full blood of an HLA A2-positive, CMV-seropositive individual was stimulated for 6 hours with either non treated or urea-treated IE1 protein or YIL peptide (representing an HLA A2-restricted CTL epitope within the IE1 protein) and activation of IE1 or YIL-specific $CD4^+$ and $CD8^+$ T cells was determined by intracellular IFN-γ staining. Cells stimulated with a control peptide, representing a murine CTL epitope within the HIV p24 protein served as negative control. The cytokine secretion from activated cells was inhibited by adding Brefeldin A for the last 4 hours of stimulation. Plots show log fluorescence intensity.

FIGS. 21A-B show the increased capacity of cyanate- and urea-carbamoylated peptides to specifically reactivate $CD8^+$ T cells in heparinised whole blood of a CMV-positive HLA A2-positive individual as shown by the flow-cytometric analyses. In these experiments, the synthetic peptide YIL (10 µg/µl in 100% DMSO) was mixed 1:1 (Vol/Vol) with either 8 M deposed urea (preincubated over night at 96° C.) or 200 mM potassium cyanate in $H_2O_{dest}$ and incubated over night at 40° C. Then, heparinized full blood of an HLA A2-positive, CMV-seropositive individual was stimulated for 9 hours with 10 µg/ml of either E10F peptide, covering a murine CTL epitope within the p24 capsid region of HIV-$1_{(BH10)}$ Gag (aa291-300) (Wild et al. (2004) Vaccine. 2004; 22:1732-1743) or YIL peptide (representing an HLA A2-restricted CTL epitope within the IE1 protein) or alternatively YIL peptide, which was carbamoylated with either 100 mM KOCN or 4 M deposed urea. For controls, cells were stimulated with either 4 mM urea or 200 mM KOCN. The activation of YIL- or PSA-specific $CD8^+$ T cells was determined by intracellular IFN-γ staining using the FACS technology. The cytokine secretion from activated cells was inhibited by adding Brefeldin A for the last 7 hours of stimulation. Plots show log fluorescence intensity.

Figure 22:
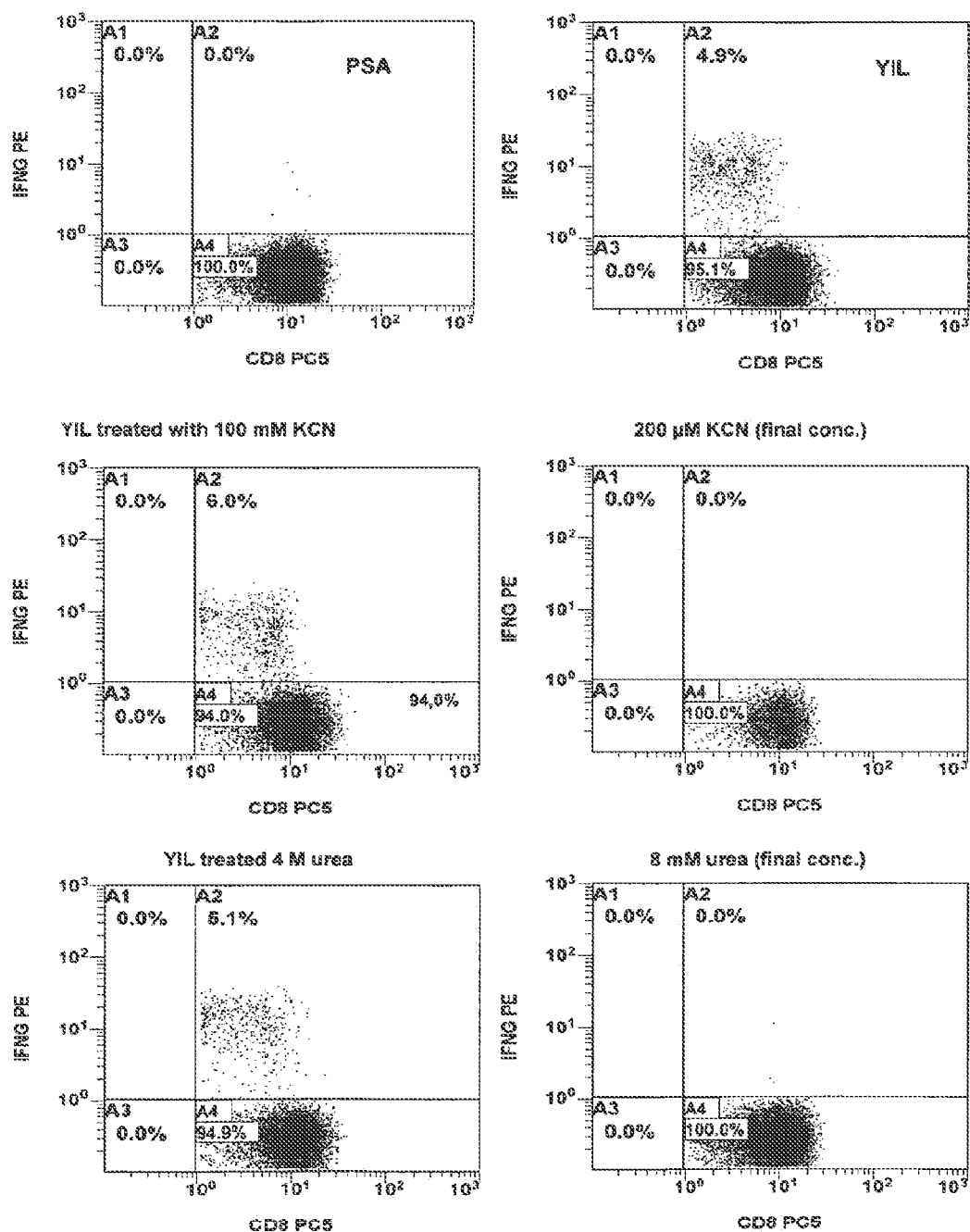

FIG. 22 shows the flow-cytometric analyses of splenic cells of mice immunized with either non modified or carbamyolated p24 in absence or presence of immunostimulatory CpG ODN 1668 after restimulation with synthetic peptides representing p24-specific CTL epitopes or non related CTL epitopes. Controls include specifically or unspecifically restimulated splenic cells of mice immunized either with PBS or HIV Gag VLP. Shown are the numbers $CD8^+$ T cells analyzed for IFN-γ secretion as determined by intracellular cytokine staining. In these experiments 6 BALB/c mice were immunized with non modified or urea-modified HIV p24 protein in absence or presence of immunostimulatory CpG ODN 1668 (Bauer et al., (1999) Immunology 97:699). For negative and positive controls, mice were immunized with PBS or HIV Gag virus-like particles (VLP) (Deml et al. 2005, Mol. Immunol. 42:259). At week two and four after the primary immunisation, mice received a booster injection with the same immunogen. 7 days after the first and second booster injection, splenic cells were obtained from each three mice per group and each $2 \times 10^6$ cells were restimulated for 6 hours with 10 µg of either a HIV C-type p24 peptide (AMQILKDTI (SEQ ID NO: 1); $aa_{197-205}$ in case of p24 immunized mice) or the $HIV_{LAI}$ A91 peptide (AMQMLKETI (SEQ ID NO: 2); $aa_{197-205}$ (Wild et al. (2004), Vaccine 22:1732)) in case of mice immunized with virus-like particles (VLP) in presence of Brefeldin A. For control, splenic cells were stimulated with a control peptide, representing a human CTL epitope within the prostate-specific antigen (PSA 141-150 FLTPKKLQCV (SEQ ID NO: 3); Chakraborty et al. (2003), Cancer Immunol. Immunother. 52:497) in presence of Brefeldin A. Shown are the mean values plus standard deviation (SD) of the numbers of IFN-γ expressing $CD8^+$ cells.

FIGS. 23A-B show the increased capacity of cyanate-carbamoylated (23A) YIL peptide and (23B) CMV pp65 protein to specifically reactivate $CD8^+$ T cells in heparinised whole blood of a CMV-seropositive HLA A2-positive individual as shown by the flow-cytometric analyses. In these experiments, synthetic YIL peptide representing an HLA A2-restricted CTL epitope within the CMV IE1 protein (YILEETSVML (SEQ ID NO: 4); amino acid 315-324; Prod'homme et al. (2003), J. Immunol. 170:2030) was dissolved in 100% DMSO with a final concentration of 2 µg/µl. The immunodominant region of CMV (strain AD169) protein pp65 (aa 862-1048; RecMol UL83-pp65, Cat. No 1B023A) was dissolved in $H_2O$ including 140 mM NaCl, 2.7 mM KCl, 10 mM $Na_2HPO_4$, 1.8 mM $KH_2PO_4$ and increasing concentrations of KOCN (0 mM, 100 mM, 200 mM and 500 mM) and incubated over night at 40° C. Then, heparinized whole blood of an HLA A2-positive, CMV-seropositive individual was stimulated for 6 hours with 10 µg/ml of indicated potassium cyanate-carbamoylated YIL peptides or pp65 proteins in presence of 0.04 M freshly prepared urea. Anti-CD49d and anti-CD28 monoclonal antibodies (BD) were added for co-stimulation according to the manufacturer's protocol. The activation YIL- or pp65-specific $CD8^+$ T cells was determined by intracellular IFN-γ staining using the FACS technology. The cytokine secretion from activated cells was inhibited by adding 10 µg/ml Brefeldin A (Sigma) for the last 4 hours of stimulation. The following reagents were used for flow cytometric analysis, unless otherwise noted: fluorescein isothiocyanate (FITC)-conjugated anti-CD8 (clone B9.11), phycoerythrin-texas-red (ECD)-conjugated anti-CD3 (clone UCHT1) and a phycoerythrin (PE)-conjugated anti-IFN-γ antibody (clone 45.15) (all Beckman Coulter). Intracellular markers were stained following staining of surface markers, fixation and permeabilisation of cells. Stained cells were run on a FACS Epics XL MCL flow cytometer (Beckman Coulter). Live-gating of lymphocytes and CD3$^+$ events was performed during acquisition. Up to $2\times10^6$ events were acquired for each analysis. Results were reported as percentage of the gated CD8$^+$ T cells producing IFN-γ in response to specific stimulation.

Generally used abbreviations for nucleotides and amino acids are used in the present invention.

The term "polynucleotide" as used herein denotes the polymeric form of nucleotides of arbitrary length, preferably deoxyribonucleotides (DNA) or ribonucleotides (RNA). The term only denotes the primary structure of the molecule. The term includes double- and single-stranded DNA or RNA, e.g. decoy or antisense polynucleotides as well as synthetic oligodeoxynucleotides (ODN) and ODN with nuclease-resistant backbone.

The term "polypeptide" or "protein" as used herein denotes a polymer of amino acids of arbitrary length. Preferably, the term "polypeptide" as used herein refers to a polymer of amino acids consisting of more than 6 amino acid residues. The term polypeptide also comprises the terms epitope, peptide, oligopeptide, protein, polyprotein and aggregates of polypeptides. Also included in this term are polypeptides which have post-translational modifications e.g. glycosylations, acetylations, phosphorylations and similar modifications as well as chemical modifications such as carbamoylations, thiocarbamoylations, substituted guanidine groups and similar modifications. This term furthermore comprises, for example, polypeptides which have one or a plurality of analogs of amino acids (e.g. unnatural amino acids), polypeptides with substituted links as well as other modifications which are state of the art, regardless of whether they occur naturally or are of non-natural origin.

The term "carbamoylation" as used herein means the transfer of the carbamoyl from a carbamoyl-containing molecule (e.g., carbamoyl phosphate) to an acceptor moiety such as an amino group, a carboxy group, a sulfhydryl group, a phosphate group, a hydroxyl group or a imidazole group. Moreover, the term "carbamoylation" as used herein further comprises the thiocarbamoylation of polypeptides.

The term "carbamoyl" as used herein means the acyl radical, $NH_2$—CO—. The transfer of the carbamoyl group plays an important role in certain biochemical reactions; e.g., in the urea cycle, via carbamoyl phosphate. The term "carbamoyl" as used herein comprises also a thiocarbamoyl group ($NH_2$—CS—).

The term "cyanate" as used herein refers to the anion NCO$^-$ derived from cyanic acid (HNCO) and any salt of cyanic acid. Moreover, the term "cyanate" as used herein refers to any organic compound containing the monovalent group —OCN and thus to any organic compound of the structure R—OCN, wherein R is any organic moiety. In particular the term "cyanate" as used herein refers also to isocyanate and isothiocyanate.

The terms "purified" and "isolated" as used herein mean that a molecule, for example, a polypeptide or a nucleic acid sequence is present in the completest possible absence of biological macromolecules of comparable type. The terms mean a fractional weight of the desired product of at least 65%, preferably of at least 75%, preferably of at least 85%, particularly preferably of at least 95% and especially preferably of at least 98% to the total weight of the biological macromolecules present. However, water, buffer and other small molecules, especially molecules having a molecular mass of less than 1000 Dalton are not included within the term "biological macromolecules" as used herein.

The term "epitope" as used herein designates the region of a polypeptide which possesses antigen properties and for example serves as a recognition site of T cells or immunoglobulins. In the sense of this invention epitopes for example are those regions of polypeptides which are recognised by immune cells such as, for example, CD4$^+$ T cells, CD8$^+$ T cells, CD4$^+$ CD8$^+$ T cells, CD4$^+$CD8$^{dim}$ T cells, CD56$^+$CD8$^+$ and CD56$^-$CD57$^+$CD8$^+$ NKT cells or CD4$^+$ regulatory T cells. An epitope can comprise 3 or more amino acids. Usually, an epitope consists of at least 6 to 7 amino acids or, which is more common, 8 to 12 amino acids, or 13 to 18 amino acids. However, an epitope may also consists of more than 18 amino acids and—even more rarely—of more than 30 amino acids. The term "epitope" as used herein also comprises a unique spatial conformation for the epitope. This spatial conformation is obtained from the sequence of amino acids in the region of the epitope.

The term "micro-organism" used here designates viruses, prokaryotic and eukaryotic microbes, such as for example archaebacteria, bacteria, single cells and fungi, wherein the latter group for example comprises yeast and filamentous fungi.

The term "immune cells" as used herein denotes lymphocytes with helper, cytolytic or regulatory properties such as, for example, CD4$^+$ T cells, CD8$^+$ T cells, CD4$^+$CD8$^+$ T cells, CD4$^+$CD8$^{dim}$ T cells, CD4$^+$ regulatory T cells, CD56$^+$CD8$^+$ and CD56$^-$CD57$^+$CD8$^+$ NKT cells as well as CD16$^+$CD56$^+$ NK cells. However, the term "immune cells" as used herein does not mean only immune cells held and multiplied in vitro in culture media but also immune cell populations taken from a healthy blood donor, patient or an animal as well as respectively purified immune cells.

The term "polypeptide-specific T cells" as used herein refers to all kind of T cells having receptors for specific binding sites of specific polypeptides as e.g. CD4$^+$ T cells, CD8$^+$ T cells and CD4$^+$ regulatory T cells. The term "polypeptide-specific T cells" as used herein comprises also epitope-specific, antigen-specific and immunogen-stimulatable cells.

The term "CD4$^+$ T cell" as used herein refers to T helper cells, which either orchestrate the activation of macrophages and CD8$^+$ T cells (Th-1 cells), the production of antibodies by B cells (Th-2 cells) or which have been thought to play an essential role in autoimmune diseases (Th-17 cells). In addition, the term "CD4$^+$ T cells" also refers to regulatory T cells, which represent approximately 10% of the total population of CD4$^+$ T cells. Regulatory T cells play an essential role in the dampening of immune responses, in the prevention of autoimmune diseases and in oral tolerance.

The terms "natural regulatory T cells" or "regulatory T cells" as used herein refer to Treg, Th3 and Tr1 cells. Treg are characterized by the expression of surface markers CD4, CD25, CTLA4 and the transcription factor Foxp3. Th3 and Tr1 cells are CD4$^+$ T cells, which are characterized by the expression of TGF-β (Th3 cells) or IL-10 (Tr1 cells), respectively.

The terms "CD8$^+$ T cell" or "CTL" as used herein refers to cytotoxic T cells recognizing and destructing degenerated, neoplastic and malignant cells as well as tissue and cells, which are infected by micro-organisms or parasites. CD8$^+$ T cell are also called CD4$^-$CD8$^+$ T cells or Th-1 cells.

The term "antigen-presenting cell (APC)" as used herein refers to cells, which are capable of capturing, processing polypeptides and presenting fragments of these polypeptides (epitopes) to the immune system in association with MHC class I and MHC class II proteins. Particularly, the term "antigen-presenting cell (APC)" as used herein refers to professional APC such as dendritic cells, monocytes, macrophages and B cells, but also to non-professional APC such as neutrophiles, fibroblasts but also vascular epithelial cells and various epithelial, mesenchymal cells as well as microglia cells of the brain.

The term "deposed urea" as used herein refers to urea being pre-treated by several incubation conditions. In particular, the pre-treatment of the urea may comprise the incubation of urea at about −20° C. to about 40° C., preferably by about room temperature for several hours, days, weeks or months and/or the heating of urea at temperatures in the range from about 40° C. to about 100° C. for several minutes, hours or days. The term "deposed urea" as used herein refers preferably to a urea solution having an increased cyanate-concentration in comparison to non-deposed urea. Preferably, the term "deposed urea" as used herein refers to a urea solution having a cyanate-concentration in the range from about 0.2 to about 50 mmol/l, more preferred in the range from about 0.3, 0.4, 0.5, 0.6, 0.7, 0.8 or about 0.9 to about 50 mmol/l, more preferred in the range from about 1 to about 50 mmol/l, more preferred in the range from about 2 to about 45 mmol/l, more preferred in the range from about 5 to about 40 mmol/l, more preferred in the range from about 10 to about 40 mmol/l, more preferred in the range from about 20 to about 40 mmol/l, more preferred in the range from about 30 to about 40 mmol/l.

The term "protein transduction domain (PTD)" as used herein refers to domains and chains of proteins which are able to translocate said proteins into the cytoplasm of cells. Thus, protein transduction domains promote the transfer of extracellular proteins into the cytoplasm of cell and in particular into the APC's endogenous pathway of processing namely the MHC class I route. In particular the term "protein transduction domain (PTD)" as used herein refers to (i) natural protein transduction domains such as arginine-rich PTDs, including HIV Tat (transactivator of transcription), Drosophila Antp (Antennapedia) and PTD-5,
(ii) hydrophobic signal sequence such as the signal sequence of fibroblast growth factor, also referred to as the membrane transduction sequence (MTS),
(iii) synthetic protein transduction domains, such as lysine, ornithine and arginine homopolymers, and
(iv) membrane translocation domains of bacterial toxins such as diphtheria toxin and tetanus toxin The inventors of the present invention have surprisingly found that polypeptides incubated with cyanate can be transferred into cells in the presence of urea with a high efficiency. Moreover, the inventors of the present invention found that the polypeptides incubated with cyanate induce a significant epitope presentation on MHC class I and II proteins in immune cells in the presence of urea and are thus able to prime, reactivate and expand polypeptide-specific T cells (e.g. CD4$^+$ T cells and CD8$^+$ T cells) efficiently.

Thus, the present invention relates to a method for polypeptide transfer into cells, comprising the following steps:

a) Incubating polypeptides in a solution comprising cyanate ions, wherein the cyanate ions are present at a concentration in the range from about 0.2 to about 9000 mmol/l, and
b) Incubating cells with the polypeptides of step (a) in the presence of urea.

The method according to the invention can be used to infiltrate polypeptides into arbitrary cells, that are prokaryotic e.g. bacteria and eukaryotic cells, e.g. fungi such as yeasts and filamentous fungi, insect cells, bird, reptile, fish, amphibian, mammalian cells e.g., murine or human cells, in particular antigen presenting cells (APC) such as dendritic cells (e.g. Langerhans cells), monocytes, macrophages, B cells but also vascular epithelial cells and various epithelial, mesenchymal cells as well as microglia cells of the brain.

Another method according to the present invention is a method for the detection of polypeptide-specific immune cells, comprising the following steps:

a) Incubating polypeptides in a solution comprising cyanate ions, wherein the cyanate ions are present at a concentration in the range from about 0.2 to about 9000 mmol/l, and
b) Incubating APC-containing cell cultures or body fluids with the polypeptides of step (a) in the presence of urea,
c) Incubating the APC-containing cell cultures or body fluids obtained according to step b) with immune cells or immune-cell-containing body fluids,
d) Simultaneously and/or specifically detecting and/or quantifying various subtypes of polypeptide-specific immune cells which are specific against the polypeptides from step a).

The APC-containing body fluid is preferably whole blood and/or liquor. In one embodiment of the method for detection according to the present invention the APC-containing cell culture comprises a PBMC population (leukapheresate), isolated monocytic cells and/or a separated APC population, preferably comprising dendritic cells (Langerhans cells), monocytes, macrophages and/or B cells. The term "APC-containing cell cultures" as used herein thus means not only cells comprising APC held and multiplied in vitro in culture media but also cell populations taken from a proband, patients or an animal and containing purified APC. For example, blood or another APC-containing body fluid can be taken from a healthy blood donor or patient. The body fluid can either be used directly in step b) of the method according to the invention or APC-containing cell populations can be purified and then used. The purification of APC-containing cell populations from blood or other APC-containing body fluids is state of the art and known to the person skilled in the art.

After incubating the APC-containing cell cultures or body fluids with the carbamoylated polypeptides in the presence of a urea solution, the cells are incubated with immune cells or immune-cell-containing body fluids. The immune cells or immune-cell-containing body fluids is preferably obtained from the same healthy blood donor, patient or animal from which the APC-containing cell cultures or body fluids originate. Alternatively, the immune cells or immune-cell-containing body fluids are obtained from healthy blood donors, patients or animals having an MHC pattern compatible with the APC-containing cell cultures or body fluids. The polypeptide-specific immune-cell-containing body fluids may be whole blood and/or liquor. The polypeptide-specific immune cells may be T cells, preferably CD4$^+$ T cells, CD8$^+$ T cells, CD4$^+$CD8$^{dim}$ T cells and/or CD4$^+$ regulatory T cells, and/or they may be other immunological cell populations, preferably CD56$^+$CD8$^+$, CD56$^-$CD57$^+$CD8$^+$ NKT cells and/or CD56$^+$ NK cells.

Methods for obtaining and purifying defined APC and immune cell populations are state of the art.

The APC-containing cell culture or body fluid, e.g. whole blood, liquor or purified PBMC used in step b) can already contain the populations of immune cells to be detected. In this case, it is no longer necessary to add immune cells or immune-cell-containing body fluids in step c).

The incubation in step c) is about 1 min to about 240 hours or longer, preferably about 2 to about 6 hours or about 6 to about 12 hours or about 12 to about 36 hours, or about 36 to 72 hours, or 72 to about 240 hours under suitable cultivation conditions, for example, at 37° C. in a humidified atmosphere with 5 to 8% $CO_2$ in T cell medium (RPMI 1640 with 2 to 10% heat-inactivated (30 min, 56° C.) human serum or foetal calf serum (FCS), 2 mM glutamine and 100 mg/ml kanamycin or gentamicin (all components from Pan-Systems, Aidenbach). However, other suitable conditions known in the art with variations in media composition, temperature, air humidity, incubation time can also be used.

The detection of defined populations of polypeptide-specific immune cells is based on the finding that after a specific recognition of polypeptides which are presented jointly with MHC proteins of classes II and/or I on the surface of APC, immune cells show an enhanced expression of characteristic cytokines, especially IFN-γ and/or TNF and/or IL-2, or IL-4 and/or IL-5, or IL-17 or IL-10 and/or TGF-β. As a result of a joint analysis of surface proteins which are characteristic of defined immune cell populations, and of cytokines, the presence and/or concentration of defined populations of polypeptide-specific immune cells can be detected from a mixture of different populations of immune cells. The detection and/or quantification in step d) thus take place via the simultaneous detection of surface proteins and cytokines.

Thus, in one embodiment of the method for detection according to the present invention the detection and/or the quantification is carried out by means of detection of specific surface markers for the polypeptide-specific immune cells and the production of marker cytokines such as IL-2, TNF, IFNγ, IL4 or IL5, IL10, TGF-β. The detection and/or quantification may be preformed by ELISA, ELISpot or FACS analysis. Alternatively, the detection and/or quantification is carried out by means of measurement of transient surface expression of CD107a,b or by means of T cell proliferation, or, if e.g. $CD8^+$ T cells are detected or quantified, by means of a classical chromium release test or an adequate non-radioactive method.

Moreover, the detection of defined cell populations via specific surface proteins may be carried out, for example via CD4 for T helper cells, CD8 for cytotoxic T cells, CD4 and CD8 for $CD4^+CD8^{dim}$ and $CD4^+CD8^+$ T cells, CD56 for NK cells, CD4 and CD25 for Treg cells and CD56 and CD8 or CD57 and CD8 for various populations of NKT cells. Specific states of the cell populations (naive versus activated cells versus memory cells) and the degree of activatability can furthermore be determined by detecting additional surface proteins (for example, CD69, CD45RO, CD45RA, CCR7) and intracellular proteins (for example, granzyme, perforin, FoxP3), intracellular cytokines (for example IL-2, TNF, IFN-γ, IL-4, IL-5, IL-10, TGF-β) or surface exposed proteins such as CD107a,b. Thus, a specific detection of specific cell populations is possible according to the method of the present invention. The listed characteristic surface markers for defined cell populations are known in the art as well as the detection and characterisation of different populations of immune cells using FACS technology for example.

The specific activation of immune cells is detected after their incubation with the APC-containing cell cultures or body fluids obtained according to step b) by measuring any increased cytokine production of the activated immune cells. For example, $CD4^+$ T cells, $CD8^+$ T cells, $CD4^+CD8^{dim}$ and $CD4^+CD8^+$ T cells, $CD56^+$ NK cells, and $CD56^+CD8^+$ or $CD57^+CD8^+$ NKT cells produce increased IFN-γ after specific stimulation, whereas $CD4^+$ T helper cells of the T helper 2 type (Th-2) show increased production of the cytokines IL-4 and IL-5. Regulatory T cells (Treg, Th3, Tr1 cells) show an increased expression of IL-10 and/or TGF-β. The cytokines produced can be determined simply by known methods in the art either intracellularly or after secretion in the supernatant using, in some cases, commercially available methods, for example FACS (e.g. by intracellular cytokine staining, or the cytokine secretion assay), ELISA or ELIspot technology. Detection is also possible by means of other cytokines produced after the specific activation of immune cells or other markers produced.

Activated immune cells can be determined and characterised for example using flow cytometry (FACS: Fluorescence activated cell scan). This method allows the fluorescence intensity of individual cells in a mixed cell population to be measured using a flow cytometer. The flow-cytometric analysis of the cells is then made using an FACS system for example a FACS Epics XL MCL flow cytometer and the Expo 32 software (Becton Coulter) or the FACS Canto II flow cytometer and the Diva 6.1.1. software (Beckton Dickinson).

Fluorescence-coupled, e.g. with R-phycoerythrin (R-PE), peridin-chlorophyll c (PerCP), fluoescein (FITC), Texas Red (TX), allophycocyanin (APC), Amcyane, Pacific Blue, Tandem PE-TX, Tandem PE-Cy5, PE-Cy7 or Tandem APC-Cy7, diverse Alexa fluorochromes, primary or secondary antibodies are suitable for detecting the characteristic surface proteins and cytokines described previously using FACS technology and are available commercially (for example, from Becton Dickinson, Dako, Coulter, eBioscience, Biolegend). In addition to the FACS method, other methods suitable for determining the production from immune cells, for example ELISA methods, Elispot methods, biosensors and expression profiling are also suitable for detecting polypeptide specific immune cells. These methods are known in the art.

Another method according to the present invention is a method for priming, expansion and/or reactivation of polypeptide-specific T cells comprising the following steps:
a) Incubating polypeptides in a solution comprising cyanate ions, wherein the cyanate ions are present at a concentration in the range from about 0.2 to about 9000 mmol/l, and
b) Incubating cells with the polypeptides of step (a) in the presence of urea and in absence or presence of immune-modulatory substances.

In said method the polypeptide-specific T cells are preferably $CD4^+$ T cells and/or $CD8^+$ T cells.

The method for priming, expansion and/or reactivation of polypeptide-specific T cells can be carried out in vivo, in vitro and/or ex vivo.

The cells incubated in step b) can be APC and/or T cells being purified from blood, peripheric blood mononuclear cells (PBMC) or other body fluid comprising said APC and/or T cells. Alternatively, blood, PBMC or other body fluid comprising APC and/or T cells is directly used in step b). The blood, PBMC or other body fluid comprising APC and/or T cells can be a sample previously obtained from a human or an animal patient.

In one embodiment of the method for priming, expansion and/or reactivation of polypeptide-specific T cells according to the present invention, the incubation of step b) is preformed several times, preferably 2, 3, 4, 5, 6, 7, 8, 9, 10 or even more times. The repetition of step b) is in particular preferred for a method for expansion of polypeptide specific T cells.

All methods according of the present invention are based on the inventive teaching that the transfer of polypeptides into cells is significantly improved if polypeptides pretreated with cyanate are incubated with said cells in the presence of urea. Thus, the following teaching refers to all methods according to the present invention as described above.

The polypeptides can be synthetically produced or expressed in various cells by means of usual pro- or eukaryotic expression systems. Example for suitable expression systems are bacteria such as *Bacillus subtilis, E. coli, Streptococcus cremoris* or *Streptococcus lividans*, yeast cells such as *Candida albicans, Candida maltosa, Hansenula polymorpha, Kluyveromyces fragilis, Saccharomyces cerevisiae, Schizosaccharomyces pombe*, or *Yarrowia lipolytica*, insect cells such as *Aedes aegypti, Autographa californica, Bombvx mori, Drosophila melanogaster, Spodoptera frugiperda*, or *Trichoplusia ni*, mammalian cells such as Chinese hamster ovary (CHO) cells, HeLa cells, baby hamster kidney (BHK) cells, monkey kidney cells (COS), or plant cells.

The polypeptides used can be purified by conventional molecular biological methods, e.g. by cell disruption, nucleic acid digestion, methods for concentrating proteins, affinity chromatography, ion exchanger chromatography and gel filtration, or in combination with polypeptide-denaturing methods e.g. acid precipitation, urea treatment, alkali treatment, heat treatment, treatment with sodium dodecylsulphate (SDS) or sonification. These methods for purifying polypeptides can furthermore be combined in an arbitrary fashion.

The polypeptides can be synthetic i.e. non-naturally occurring polypeptides or they can occur in arbitrary living beings, e.g. in mammals such as humans, primates, mouse, rat, rabbit, goat, sheep, cow, pig or in any animals, parasites, micro-organisms or viruses. However, they can also originate from plants and algae. In addition, they can originate from prion proteins.

Polypeptides being used in step a) of the methods according to the present invention can be divided in two groups regarding their intrinsic property to enter the cytosol of cells, in particular APC.

The first group of polypeptides has an intrinsic property to enter the cytosol of cells, in particular APC. Such proteins are therefore processed and presented via the MHC class I route without any further aids. Said intrinsic property may be caused by a transduction domain (PTD) of said protein. Said transduction domain may be a naturally existing transduction domain (PTD) or a recombinantly added transduction domain. Examples for proteins having a naturally existing transduction domain are the HIV transactivator of transcription (Tat) and Rev protein, herpes simplex virus VP22 and the Drosophila antennapedia homeoprotein (antp) (Sugita et al. (2008) Br J Pharmacol. 153: 1143-1152). However, said intrinsic property may also be caused by an intrinsic function of a specific chain of the polypeptide such as the heavy chain of the tetanus toxin. Other examples for polypeptides having intrinsic function to enter the cytosol of cells are toxins such as the diphtheria toxin. Here, translocation is mediated by a translocation or "T domain". In addition, a hydrophobic signal sequence of the fibroblast growth factor, also referred to as the membrane transduction sequence (MTS), has been demonstrated to be another type of cell-penetrating peptide (CPP). In addition, coupling of polypeptides to micro beads, antibodies, lipids, heat shock proteins and arginine-rich protein transduction domains (PTD) confers delivery to the HLA class I processing machinery of APC.

The second group of polypeptides has no intrinsic property to enter the cytosol of cells, in particular APC. Such proteins do not enter the cytosol of APC without any aid but remain in the endosomal/endolysosomal compartments of said APC. Consequently, said proteins are normally not processed and presented via the MHC class I route but are processed and presented via the MHC class II route only. The second group includes the vast majority of naturally occurring and recombinant made human, microbial, viral, animal or vegetable proteins and in particular respective soluble polypeptides and polypeptides of lysates of cells, tissues, bacteria, viruses and parasites.

In one embodiment of the present invention the methods of the present invention are carried out with polypeptides of the first group as described above and thus with polypeptides having an intrinsic property to enter the cytosol of cells, in particular APC. Thereby, the methods of the present invention further promote the transfer of the polypeptides into the cytosol of cells, in particular APC. Thus, the efficiency of polypeptide transfer can be increased for said polypeptides by the methods according to the present invention.

In another embodiment of the present invention the methods of the present invention are carried out with polypeptides of the second group as described above and thus with polypeptides having naturally no intrinsic property to enter the cytosol of cells, in particular APC. For such polypeptides the present invention provides a method for very efficient polypeptide transfer into the cytosol of cell, in particular APC.

Preferred polypeptides of the second group are all kind of polypeptides having T cell epitopes but lacking (i) a natural protein transduction domain and/or (ii) any vector or domain linked to said polypeptide recombinantely which causes translocation of the polypeptide into cells, in particular APC.

Examples for polypeptides of the second group are microbial proteins, in particular proteins of
 (i) Human immunodeficiency virus (HIV) such as gp120, gp160, p24, gag, polymerase, reverse transkriptase and nef,
 (ii) Epstein-Barr virus (EBV) such as EBNA1, EBNA2, EBNA3A, EBNA3B, EBNA3C, EBNA4, EBNA6, BZLF1, BMLF1, BMRF1, BHRF1, BARF0, BRLF1, BI'LF4, gp85, gp110, gp220/350, VCA p150, EBNA-LB, LMP-1 and LMP-2 (e.g. described in Khanna et al. (2000), *Annu. Rev, Microbiol.* 54:19-48),
 (iii) Cytomegalovirus (CMV) such as UL123 (IE1), UL122 (IE-2), UL83 (pp65), UL82, HL99, UL28, UL33, UL37, US3, UL94, UL16, UL55(gB), UL85, UL25, US18, UL45 and UL32 (pp150) (e.g. described in Crough et al. (2009) *Clin Microbiol Rev.* 22:76-98),
 (iv) Varicella zoster virus (VZV) such as ORF1, ORF4, ORF10, ORF14, ORF29, ORF62 and ORF68 (gE),
 (v) *M. tuberculosis* such as CFP10, ESAT6, TB7.7, TB37.6, MPT63
 (vi) *Borrelia burgdorfer* such as OSP A and OSP C
 (vii) Hepatitis B virus such as HBsAg and HBcAg, and
 (viii) Adenovirus such as AdV5 Hexon In addition, human proteins are preferred polypeptides of said second group for example tumor antigens such as prostate-specific antigen (PSA), HER-2/neu, MUC-1, point mutated or wild-type overexpressed p53, MAGE antigen and CEA (carcinoembryonic antigen). Also proteins representing relevant targets for autoaggressive T cells in autoimmune diseases are preferred polypeptides of said second group. Examples for such proteins in regard to the autoimmune disease multiple sclerosis are myelin basic protein (MBP), myelin oligodendrocyte glycoprotein (MOG), proteolipid protein (PLP), Myelin, MBP/PLP fusion protein (MP4), myelin-associated glycoprotein (MAG). Examples for such proteins in regard to the autoimmune disease type I diabetes are insulin B, pre-pro-insulin (PPI), IA-2, GAD65, IGRP, cd4, chromogranin A (ChgA) (as e.g. described in Velthuis et al. (2010) *Diabetes*). Also preferred is the use of fragments of the above mentioned proteins for the methods according to the present invention.

To determine whether a polypeptide is a polypeptide of the first or the second group as described above the ability of entering the cytosol of eukaryotic cells, in particular APC, can be tested e.g. by means of fluorescence microscopy, where cell compartments and polypeptides can be fluorescence-conjugated. Respective methods are known by a person skilled in the art and are e.g. described in Kaplan et al. (Journal of Controlled Release 102 (2005) 247-253) and in WO 99/55899.

The polypeptides of step a) in the methods according to the present invention can be used in any arbitrary concentrations. Preferably, the concentration lies in the range from about 0.01 to about 200 μg/ml or higher, in the range from about 0.01 to about 0.1 μg/ml, in the range from about 0.1 to about 0.5 μg/ml, in the range from about 0.5 to about 2 μg/ml, in the range from about 2 to about 10 μg/ml, in the range from about 10 to about 50 μg/ml or in the range from about 50 to about 200 μg/ml. Most preferred are polypeptide concentrations from about 0.1 to about 50 μg/ml, more preferred in the range from about 1 to about 40 μg/ml, from about 3 to about 30 μg/ml, or from about 5 to about 20 μg/ml. Especially preferred is a polypeptide concentration of about 10 μg/ml.

The pre-treatment of polypeptides with cyanate in step a) in the methods according to the present invention results in a carbamoylation of amino groups of the polypeptides. A carbamoylation is the transfer of the carbamoyl from a carbamoyl-containing molecule (e.g., carbamoyl phosphate) to an acceptor moiety such as an amino group, a carboxy group, a sulfhydryl group, a phosphate group, a hydroxyl group or a imidazole group. A carbamoyl is an acyl radical having the structure $NH_2$—CO—. However, the carbamoylation may also occur by a thiocarbamoyl group having the structure $NH_2$—CS—.

The carbamoylation of the polypeptide according to the present invention can be a carbamoylation of an amino group, a carboxy group, a sulfhydryl group, a phosphate group, a hydroxyl group or an imidazole group. Preferably the carbamoylation of the polypeptides according to the present invention is a carbamoylation of the primary amino groups of the polypeptide, in particular of the terminal amino group and the epsilon-amino group of lysine residues. Alternatively or in addition, the hydroxyl group of tyrosine, the sulfhydryl group of cysteine, the carboxyl group of aspartic and glutamic acids and the imidazole group of histidine can be carbamoylated.

Carbamoylation reaction can be performed by incubating polypeptides in a solution comprising cyanate. In one embodiment of the present invention the cyanate concentration is in the range from about 0.3 to about 5000 mmol/l, more preferably in the range from about 0.4, 0.5, 0.6, 0.7, 0.8 or about 0.9 to about 5000 mmol/l, in the range from about 1, 2 or about 5 to about 5000 mmol/l, in the range from about 2 to about 5000 mmol/l, in the range from about 10 to about 4000 mmol/l, in the range from about 25 to about 3000 mmol/l, in a range from about 100 mmol/l to about 2000 mmol/l or in the range from about 500 mmol/l to about 1000 mmol/l. Most preferred are cyanate concentrations in the range from about 1 mmol/l to about 1000 mmol/l, more preferred in the range from about 5 mmol/l to about 900 mmol/l, from about 10 mmol/l to about 800 mmol/l, from about 20 mmol/l to about 700 mmol/l or from about 50 mmol/l to about 600 mmol/l. In particular, cyanate concentrations from about 100 mmol/l to about 500 mmol/l are preferred, such as cyanate concentration of about 100 mmol/l, about 150 mmol/l, about 200 mmol/l, about 250 mmol/l, about 300 mmol/l, about 350 mmol/l, about 400 mmol/l, about 450 mmol/l or about 500 mmol/l.

The incubation time of step a) of the methods according to the present invention can be about several minutes up to several hours, days, weeks or months. The incubation may occur at temperatures in the range from about −20° C. to about 100° C., preferably in the range from about room temperature to about 96° C. or in the range from about 40° C. to about 96° C. Incubation at a low temperature requires a longer incubation time and incubation at a high temperature requires a shorter incubation time, in particular because polypeptides degrade if they are incubated at high temperatures for a long time. Preferred is an incubation temperature in the range from about room temperature to about 60° C., in the range from about 30° C. to 50° C. or in the range from about 37° C. to 45° C. Especially preferred is an incubation temperature of about 40° C. Thereby an incubation time of about 5 minutes to about 24 h or of about 30 minutes to about 2 hours is preferred. Especially preferred is an incubation time of about 1 hour.

In one embodiment of the present invention the polypeptide is incubated for carbamoylation in a urea solution comprising cyanate. Preferably the urea concentration of said urea solution is in the range from about 0.01 mol/liter to about 8 mol/liter, from about 0.1 to about 0.5 mol/liter, from about 0.5 to about 5 mol/liter or from about 5 to about 8 mol/liter.

The cyanate concentration of a freshly prepared urea solution is less than 0.2 mmol/l. However, according to step a) of the methods according the present invention the polypeptides have to be incubated in a solution having a cyanate concentration of at least 0.2 mmol/l. Preferred is a solution comprising urea with a cyanate concentration in the range from about 0.2 to about 50 mmol/l, more preferred in the range from about 0.3, 0.4, 0.5, 0.6, 0.7, 0.8 or about 0.9 to about 50 mmol/l, from about 1 to about 50 mmol/l, from about 2 to about 45 mmol/l, from about 5 to about 40 mmol/l, from about 10 to about 40 mmol/l, from about 20 to about 40 mmol/l or from about 30 to about 40 mmol/l.

For increasing the cyanate concentration of a urea solution there are several possibilities.

In one embodiment of the present invention the cyanate concentration of the urea solution is increased by the incubation of said urea solution under specific incubation conditions. Urea in solution is in equilibrium with ammonium cyanate. The form that reacts with amino groups of polypeptides is isocyanic acid. Isocyanic acid reacts with the amino terminus of polypeptides and the side chains of lysine and arginine residues. Thus, the carbamoylation of polypeptides in a urea solution can be enhanced by an increase of the cyanate concentration of said urea solution and thus by a manipulation of the equilibrium reaction of urea and ammonium cyanate. Said equilibrium reaction can be influenced by heat and/or by incubation time.

Cyanate accumulation in aqueous solutions of urea has been analysed in detail by Marier and coworkers (Marier et al. (1964) *Analytical Biochemistry* 7:304). They described, that a maximum cyanate level was reached at 25° C. in about 60 days. At a given urea concentration, the maximum cyanate level at 25° C. was approximately 60% of that obtained at 38° C. (7 days) and approximately 23% of that obtained at 85° C. (50 min).

For increasing the cyanate concentration of the urea solution the urea solution can be incubated about several minutes up to several hours, days, weeks or months. The incubation may occur at temperatures in the range from about −20° C. to about 100° C., from about room temperature to about 98° C., from about 37° C. to about 96° C., from about 40° C. to about 96° C., or from about 70, 80 or about 90 to about 96° C. For increasing the cyanate concentration it is apparent that incubation at a low temperature requires a long incubation temperature, wherein incubation at a high temperature requires a shorter incubation time. For example, incubation at −20° C. may require an incubation time of about several weeks up to several months, wherein incubation at 96° C. may require an incubation time of about several minutes, up to about 1 hour or several hours.

If a pretreated urea-solution as described above is used in the incubation of step a) in the methods according to the present invention, the incubation of step a) occurs preferably at temperatures in the range from about room temperature to about 100° C., from about 30° C. to about 70° C., or from about 37° C. to about 40° C. Thereby, an incubation time of about 5 minutes to about 48 hours is preferred. However, more preferred is an incubation time of about 30 minutes to about 24 hours.

In another embodiment of the present invention the cyanate concentration of the urea solution is increased during the incubation step a) of the methods according to the present invention. Therefore, the polypeptide can be incubated in the urea solution about several minutes up to several hours, days, weeks or months. The incubation may occur at temperatures in the range from about −20° C. to about 100° C., from about room temperature to about 96° C. or from about 40° C. to about 96° C. For increasing the cyanate concentration it is apparently, that incubation at a low temperature requires a long incubation temperature, wherein incubation at a high temperature requires a shorter incubation time. However, the degradation of the polypeptide at higher temperatures has also to be considered. Preferred are for example incubation times from about 20 minutes to about 4 hours, or from about 30 minutes to about 2 hours. Especially preferred is an incubation time of about 1 hour at a temperature of about 96° C. Also preferred are incubation times from about 1 h to 3 h, preferably 2 h at temperatures from about 60 to about 90° C., especially preferred from about 70 to about 80° C.

Suitable incubation conditions for increasing the cyanate concentration of a urea-solution alone or a urea-solution comprising polypeptides can be identified by measuring the cyanate concentration. Methods for measuring the cyanate concentration of solutions are known in the art by a person skilled in the art (see e.g. Marier et al. (1964) *Analytical Biochemistry* 7:304).

The pH-value of step a) in the methods according to the present invention is preferably from about 3.0 to about 9.0, more preferably about 3.9, 6.8 or 8.7. In particular, the carbamoylation of phosphate groups can be increased by the increase of the pH-value. However, the carbamoylation of lysine groups occurs preferably at an acidic pH-value.

In still another embodiment of the present invention the carbamoylation of the polypeptide is achieved by strategies for a quantitative carbamoylation of polypeptides described by Angel and coworkers (Angel et al. (2007) *Rapid Commun. Mass Spectrom.* 21:1623). Accordingly, polypeptides are dissolved in 100 μl 8 M urea, 200 mM Tris-HCl, pH 7.4. This solution is reduced with 20 mM dithiothreitol (DTT) for 2 hours at 50° C., followed by carbamidomethylation with 45 mM iodoacetamide (IDA) at room temperature for 1 hour. The solution of denatured, reduced, and alkylated polypeptides is diluted 1:8 with 50 mM ammonium bicarbonate to adjust the concentration of urea to 1 M and incubated overnight at 37° C. After digestion, the solution is dried and dissolved in 300 μl 8 M urea, 200 mM Tris-HCl, pH 8.5. Then samples are vortexed until complete solubilization and then incubated for 4 h at 80° C., with periodic vortexing of the samples.

In one embodiment of the present invention cyanate is added to the urea solution of step a) of the methods according to the present invention. Thereby, final cyanate concentrations in the range from about 1 mmol/l to about 1000 mmol/l are preferred. More preferred are cyanate concentrations in the range from about 5 mmol/l to about 900 mmol/l, from about 10 mmol/l to about 800 mmol/l, from about 20 mmol/l to about 700 mmol/l or from about 50 mmol/l to about 600 mmol/l. In particular, cyanate concentrations from about 100 mmol/l to about 500 mmol/l are preferred, such as cyanate concentration of about 100 mmol/l, about 150 mmol/l, about 200 mmol/l, about 250 mmol/l, about 300 mmol/l, about 350 mmol/l, about 400 mmol/l, about 450 mmol/l or about 500 mmol/l.

In one embodiment of the present invention the carbamoylation of the polypeptide of step a) can be achieved by the incubation of the polypeptide with alkali metal cyanate, an organic isocyanate or an organic isothiocyanate in an alkaline medium. The incubation time can be from several minutes to about 36 hours, preferably from about 30 minutes to about 24 hours, preferably from about 1 hour to about 12 hours. The incubation temperature is preferably at least about 20° C., about 30° C., about 40° C. or about 50° C. The pH-value is preferably from about 7 to 11, more preferably from about 8 to about 10. Preferred is the use of potassium cyanate, sodium cyanate, silver cyanate or β-Estradiol 6 oxime (a BSA fluorescein isocyanat conjugat).

The carbamoylated polypeptides are then used for incubating the cells in step b) of the methods according to the present invention. The amount of polypeptide used for approximately $10^6$ cells should be in the range from about 0.1 to about 200 μg or higher, from about 0.1 to about 200 μg, from about 0.1 to about 2 μg, from about 0.1 to about 10 μg, from about 10 to about 50 μg or from about 50 to about 200 μg of polypeptide.

In one embodiment of the methods according to the present invention the urea concentration in step b) is in the range from about 0.001 to about 0.8 mol/L, preferably in the range from about 0.001 to about 0.2 mol/L, from about 0.001 to about 0.1 mol/L, from about 0.001 to about 0.01 mol/L, from about 0.01 to about 0.2 mol/L, frm about 0.01 to about 0.1 mol/L or from about 0.1 to about 0.8 mol/L. However the urea concentration can also be less than 0.001 mol/L. If there is a high total number of living cells and a ratio of living to dead cells where the living cells predominate, the urea concentration in step b) should be less than about 0.8 mol/L, preferably less than about 0.3 mol/L. Most preferred is a urea concentration in step b) in the range from about 0.01 mol/L to about 0.1 mol/L, from about 0.015 mol/L to about 0.09 mol/L, from about 0.02 mol/L to about 0.08 mol/L, from about 0.025 mol/L to about 0.07 mol/L, from about 0.03 mol/L to about 0.06 mol/L or from about 0.035 mol/L to about 0.05 mol/L. Especially preferred is the urea concentration in step b) of about 0.04 mol/L.

Moreover, the urea solution of step b) of the methods according to the present invention may additionally comprise NaCl, preferably with a concentration in the range from about 0.25 mmol/L to about 200 mmol/L, or from about 0.25 mmol/L to about 75 mmol/L. Alternatively or in addition the urea solution of step b) of the methods according to the present invention may comprise DTE or DTT, preferably with a concentration in the range from about 0.25 nmol/L to about 200 nmol/L, or from about 0.25 nmol/L to about 75 nmol/L. Furthermore, the DTE or DTT concentration can be less than 0.25 nmol/L or greater than 200 nmol/L.

The carbamoylated polypeptides are incubated with the cells in step b) of the present invention preferably for about 1 min to about 240 hours or longer, preferably for about 2 to about 6 hours or for about 6 to about 12 hours or for about 12 to about 36 hours, or for about 36 to about 240 hours.

In another embodiment of the methods according to the present invention the incubation of step b) is preformed in a medium comprising LPS. The LPS-activity in step b) is preferably in the range from about 0.001 to about 10000 U/mL, from about 0.01 to about 8000 U/mL, from about 0.2 to about 6000 U/mL, from about 1 to 1000 U/mL, or from about 10 to 100 U/mL.

The incubation of the polypeptides in step a) results in an increase of the polypeptide's molecular weight and/or a shift of the polypeptide's pKi-value to a more acidic $pK_i$-value.

To determine if the treated polypeptides of step a) are carbamoylated and exhibit an increased molecular weight in comparison to non carbamoylated polypeptides, standard methods known by a person skilled in the art can be used. For example the comparison of the molecular weight can be analysed by a separation on a SDS-PAGE, a MALDI-TOF MS (matrix-assisted laser desorption/ionisation-time of flight mass spectrometry) analysis or NMR spectroscopy (nuclear magnetic resonance spectroscopy).

The MALDI-TOF MS is a technique, in which a co-precipitate of an UV-light absorbing matrix and a biomolecule is irradiated by a nanosecond laser pulse. Most of the laser energy is absorbed by the matrix, which prevents unwanted fragmentation of the biomolecule. The ionized biomolecules are accelerated in an electric field and enter the flight tube. During the flight in this tube, different molecules are separated according to their mass to charge ratio and reach the detector at different times. In this way each molecule yields a distinct signal. The method is used for detection and characterization of biomolecules, such as proteins, peptides, oligosaccharides and oligonucleotides, with molecular masses between 400 and 350,000 Da.

For example the comparison of the $pK_i$ values can be analysed by a two-dimension electrophoresis.

The method for detecting polypeptide-specific T cells according to the invention is suitable for many different scientific and medical applications, e.g. in analysis, diagnosis and therapy. Using the method according to the invention, different populations of polypeptide-specific immune cells can be identified at the same time, for example, for monitoring the efficiency of therapeutic and prophylactic vaccinations for inducing immune cells, for determining the efficiency of therapeutic treatments of diseases involving immune cells, for screening the safety and efficiency of medicaments which cause deletion of anergy of immune cells or bring about a general immune suppression, for monitoring and diagnosis of diseases induced by microorganisms and parasites involving immune cells, for monitoring and diagnosis of chronic inflammations involving immune cells, for monitoring and diagnosis of tumour-antigen-specific immune cells, for monitoring and diagnosis of immune cells which play a role in transplant rejection, for the diagnosis of autoimmune diseases or for the specific selection of blood donors for vaccine trials and the testing of therapeutic treatments. Preferably, the method for detection according to the present invention is carried out in vitro or ex vivo.

The method according to the invention can be used in all vertebrates which have immune cells, especially T cells, especially in humans, primates and rodents. Polypeptide-specific immune cells can be detected and quantified for example from patients suffering from a microbial infection, a tumour disease, a chronically inflammatory disease, a transplant rejection or an autoimmune disease or however from healthy blood donors or participants of therapeutic or preventive trials.

In addition, epitope-specific T cells can be detected using cells obtained by the method according to the invention, preferably using APC obtained in primates or other animals which possess epitope-specific immune cells.

The method for detecting polypeptide-specific immune cells according to the present invention can be used for the diagnosis of microbial infections, autoimmune diseases, transplant rejection and tumors.

In contrast to the methods for the detection of polypeptide-specific immune cells described so far, the method according to the invention is characterised by the following advantages:
(1) Different populations of polypeptide-specific immune cells can be detected at the same time.
(2) Detection of different populations of polypeptide-specific immune cells can be carried out with small sample volumes.
(3) The quantity and quality of different populations of polypeptide-specific immune cells can be detected at the same time.
(4) The method can easily be carried out using commercially available equipment (FACS, ELISA-, ELISpot reader) routinely used in many diagnostic laboratories.
(5) The method can be universally used to detect reactive polypeptide-specific immune cells regardless of the HLA constellation of the blood donor/patient.
(6) The diagnostic method according to the invention is suitable for the patient-specific determination of lymphocyte reactivity against a complex polypeptide. In this case, it is not necessary to know target structures of these immune cells to carry out the method.
(7) Compared to the conventional diagnostic methods based on the stimulation of T cells with peptides, soluble proteins, cell lysates, expression plasmids or RNA, this method of detection for polypeptide-specific immune cells can be used universally, is easier to handle, is significantly cheaper, is less time-consuming and more sensitive.

The method for the improved priming, expansion and/or reactivation of polypeptide-specific T cells according to the present invention can be used for diagnostic, therapeutic and preventive applications. In particular the reactivation of polypeptide-specific T cells is the most important step for the detection and/or quantification of polypeptide-specific T cells for diagnostic purposes. In contrast, the expansion of polypeptide-specific T cells can be used for the preparation of cells for therapeutic application or for research purposes.

In particular the polypeptides obtained in step a) according to the methods of the present invention can be used for the priming and reactivation of polypeptide-specific T cells in vivo for e.g. the treatment or prevention of diseases. Preferably the polypeptides obtained in step a) according to the methods of the present invention can be used as prophylactic or therapeutic vaccine. Therefore, the polypeptides of step a) according to the methods of the present invention are preferably dialysed against a buffer containing urea, preferably in the range from about 0.001 to about 0.2 mol/L, more preferably in the range from about 0.01 to about 0.1 mol/L. Moreover, the buffer comprises preferably PBS. More preferably said buffer does not comprise bivalent ions.

Thus, the present invention further relates to a pharmaceutical composition comprising polypeptides obtained in step a) and preferably dialysed as described above in a buffer containing urea, preferably in the range from about 0.001 to about 0.2 mol/L, more preferably in the range from about 0.01 to about 0.1 mol/L. Moreover, the buffer comprises preferably PBS. More preferably said buffer does not comprise bivalent ions. Moreover, the pharmaceutical composition preferably comprises adjuvants or immunostimulatory substances. Preferably, the pharmaceutical composition is suitable for administration to a subject, preferably by injection. The pharmaceutical composition can preferably be used as a vaccine or for the treatment or prevention of infectious diseases and/or tumors.

Moreover, the present invention relates to the use of cells obtained according to the methods according to the present invention for different applications. The cells treated using the methods according to the invention can be used in the area of research, diagnostics and treatment and prevention of diseases in animals and humans. For example, the APC obtained using the method according to the invention is suitable for prophylactic and therapeutic applications for combating infectious diseases and tumours.

A further aspect of the present invention relates to the use of the methods according to the present invention in a plurality of different scientific, medicinal and diagnostic applications, e.g. for
(a) studying the importance of these polypeptides in cellular processes,
(b) inducing humoral and cellular immune responses in experimental animals and in humans,
(c) obtaining sera and antibodies for diagnostic, therapeutic and preventive applications,
(d) inducing suitable immune responses to protect against or for the treatment of microbial infections and tumour diseases,
(e) prophylactic and therapeutic vaccines or
(f) the ex vivo stimulation of T cells for diagnostic, therapeutic and preventive purposes,
(g) the identification of novel target structures (epitopes) of cytotoxic T cells.

Thus, the present invention relates to the use of carbamoylated polypeptides for inducing specific T-cells in animals, especially in mammals, e.g., in mice, rats, rabbits, sheep, goats, horses, cattle, pigs, dogs, cats and primates. The carbamoylated polypeptides can also be used for inducing cellular immune responses in humans. In this case, the carbamoylated polypeptides can either be administered alone or in combination with immune-stimulating agents ("adjuvants") or immune-modulatory substances (e.g. lipopolysaccharide (LPS)) and/or in combination with urea.

Especially suitable adjuvants and immune-modulatory stimulating agents for enhancing the efficiency of the vaccines/vaccine combinations described include, for example: (1) gel-like adjuvants such as aluminium salts (Alum), such as aluminium hydroxide, aluminium phosphate, aluminium sulphate and calcium phosphate; (2) microbial adjuvants such as bacterial nucleic acids and synthetic oligodeoxynucleotides (ODN) including CpG motifs (e.g. CpG 1668 or CpG 2216; (Waibler et al. (2008), *Europ. J. Immunol.* 38:3127), endotoxins such as, for example, monophosphoryl lipid A, exotoxins such as for example, the diphtheria, cholera, tetanus toxoid, the heat-labile enterotoxin of *E. coli* and muramyl dipeptides such as, for example, MDP; (3) oil emulsions and emulsion-based vaccines such as, for example, incomplete Freund's adjuvant (IFA), MF59, SAF and Ribi™ adjuvant system (RAS), (Ribi Immunochem, Hamilton, Mont.); (4) particular adjuvants such as, for example, immune-stimulatory complexes (ISCOMs), liposomes, PLG polymers, biologically degradable microspheres and saponins (QS-21), and synthetic adjuvants such as non-ionic block polymers, muramyl peptide analogues, polyphosphazene and synthetic polynucleotides and (5) cytokines, such as for example interleukins (IL-1, IL-2, IL-12 among others.), granulocyte/macrophage colony-stimulating factor (GM-CSF) or macrophage colony stimulating factor (M-CSF), as well as the tumour necrosis factor (TNF). In addition to adjuvants, all other substances which have an immune-stimulating effect to enhance the efficiency of the vaccine compositions described can be used. A listing of suitable available adjuvants has been compiled and can be retrieved via the world wide web at the following address (http://www.bvl.bund.de/nn_510850/EN/04_PlantProtection Products/03_PlantResistanceImproversAndAdjuvants/04_ListAdjuvants/ListAdjuvants_node.html_nnn=true).

The vaccine combinations described (e.g., carbamoylated polypeptides in conjunction with a pharmaceutically accepted carrier component and/or an adjuvant) are added to the dilution solutions, such as for example, water, salt solutions, glycerol, ethanol. In addition, additional accessory components such as moistening and emulsifying agents, pH-buffering substances and similar components can be present in these compositions.

The vaccine combinations can be combined in prime-boost regimens with other vaccines e.g. peptides, recombinant proteins, DNA expression plasmids, recombinant viruses and bacteria and live attenuated pathogens. These vaccine combinations are usually present in injectable form, either as liquid solutions or suspensions.

The immunogen composition can equally be emulsified or incorporated in liposomes in order to achieve enhanced adjuvant properties in the sense of a pharmaceutically accepted carrier component. The vaccine composition can be administered by suitable administration routes. Possible among others in this case are oral, topical, intravenous, intraperitoneal, intramuscular, intra-articular, subcutaneous, intranasal, intradermal or dermal administration routes. The vaccine composition is used in the appropriate dosage for the indication. The determination of an appropriate dosage for various organisms is state of the art. The vaccine combinations described can either be used prophylactically or therapeutically. Furthermore, APC modified using carbamoylated polypeptides are suitable for therapeutic and preventive applications. Methods for obtaining and ex vivo expansion of APC, as well as for reinfusion of ex vivo modified APC in an organism have been published on many occasions and are state of the art.

The invention is explained using the following examples but is not restricted to these:

EXAMPLE 1: CARBAMOYLATION OF POLYPEPTIDES BY TREATMENT WITH UREA AT HIGH TEMPERATURES

Purified HIV capsid protein p24 (0.84 mg/ml; dissolved in 150 mM NaCl, 50 mM NaP, pH 7.6), commercially available bovine serum albumine (BSA; albumine fraction V, Applichem); (1 mg/mL in $H_2O$) or parvovirus B19 VP2 particles (Lindner et al. (2008), *Journal of Infectious Dis-* eases, 198:1677); (0.64 mg/ml dissolved in 38% (w/v) CsCl) were mixed 1:1:1 (vol/vol/vol) with either H$_2$O and 30 mM Tris pH 3.9 or 6 M freshly prepared urea-solution and 30 mM Tris pH 3.9 and then incubated for 60 min at 96° C. on a thermoshaker (300 rpm). Then, proteins were separated by 12.5% (HIV p24) or 10% SDS-polyacrylamide gel electrophoresis (PAGE) (BSA, Parvovirus B19 VP2) and proteins were visualized by means of Coomassie brilliant blue staining. Separation of proteins by SDS PAGE and staining of proteins was performed as described in the laboratory manual "Molecular cloning: A laboratory manual, third edition (Sambrook et al. (2001), Cold Spring Harbor Laboratory, New York).

These experiments showed, that incubation with urea at high temperatures results in a chemical modification of polypeptides, as shown by an altered migration behaviour in SDS polyacrylamide gels. Herein different polypeptides e.g. HIV p24, BSA and parvovirus B19 VP2 revealed striking differences in the observed mass shift, depending on the number of carbamoylation sides and the efficiency of carbamoylation.

EXAMPLE 2: CARBAMOYLATION OF POLYPEPTIDES BY DIFFERENT CARBAMOYLATION PROTOCOLS

Commercially available BSA (1 mg/mL in H$_2$O) was mixed 1:1:1 (vol/vol/vol) with H$_2$O/HCl (pH 3.6) and 30 mM Tris pH 3.6 or with 6 M urea-solution and 30 mM Tris pH 3.6 and samples were incubated for 0 min, 30 min or 60 min at 96° C. on a thermoshaker (300 rpm). Alternatively, BSA was treated following a protein carbamoylation protocol described by Angel and coworkers (Angel et al. (2007) *Rapid Commun. Mass Spectrom.* 21:1623). 10 nmol BSA was dissolved in 100 µl 8 M urea/200 mM Tris-HCl, pH 7.4. This solution was reduced with 20 mM dithiothreitol (DTT) for 2 hours at 50° C., followed by carbamidomethylation with 45 mM iodoacetamide (IDA) at room temperature for 1 hour. The solution of denatured, reduced, and alkylated proteins were diluted 1:8 with 50 mM ammonium bicarbonate to adjust the concentration of urea to 1 M and incubated over night at 37° C. Then, the solution was dried and dissolved in 300 µl 8 M urea/200 mM Tris-HCl, pH 8.5. Then samples were vortexed until complete solubilization and then incubated for 4 hours at 80° C., with periodic vortexing of the samples (Angel et al. (2007) *Rapid Commun. Mass Spectrom.* 21:1623). Then, carbamoylated proteins were separated by 10% SDS-polyacrylamide gel electrophoresis (PAGE) and visualized by means of Coomassie brilliant blue staining.

This study shows that incubation of BSA with urea following different carbamoylation protocols results in a varying efficiency of protein carbamoylation. Herein, incubation of BSA with urea at 96° C. for 60 min induces a more efficient carbamoylation of BSA than urea-treatment for 30 min as shown by a reduced migration in SDS polyacrylamide gels. Compared with the treatment with deposed urea at high temperatures, the carbamoylation protocol by Angel and coworkers induced a more efficient carbamoylation of BSA. However, the protocol by Angel and co-workers resulted in an increased degradation of BSA. The results of these experiments demonstrate that the efficiency of polypeptide carbamoylation can be controlled using different carbamoylation protocols, thereby varying the starting products and/or the incubation time.

EXAMPLE 3: CARBAMOYLATION OF BSA WITH UREA FOLLOWING DIFFERENT CARBAMOYLATION PROTOCOLS RESULTS IN MODIFIED BSA PROTEINS REVEALING AN ALTERED pK$_I$ VALUE

Commercially available BSA (1 mg/ml in H$_2$O) was mixed 1:1:1 (vol/vol/vol) with H$_2$O/HCl (pH 3.6) and 30 mM Tris pH 3.6 or with 6 M urea-solution and 30 mM Tris pH 3.6 and samples were incubated for 0 min, 30 min or 60 min at 96° C. Alternatively BSA was treated following a protein carbamoylation protocol described by Angel and coworkers (Angel et al. (2007) *Rapid Commun. Mass Spectrom.* 21:1623) as described in example 2. Then, modified BSA proteins were separated by isoelectric focusing on IEF strips at 26350 Vh followed by a 10% SDS-PAGE electrophoresis and proteins were visualized by silver staining. 2-D electrophoresis was performed as essentially described in the hand book "Immobiline® DryStrip Kit for 2-D electrophoresis with Immobiline® DryStrip and ExcelGel SDS" 18-1038-63 Edition AB (Pharmacia Biotech) using the Multiphor II Electrophoresis System (Pharmacia) and the Electrophoresis Power Supply EPS 3500 XL.

These experiments demonstrate that chemical modification of BSA results by different carbamoylation protocols lowers the isoelectric point of BSA. Herein the reduction of the isoelectric point correlates with the degree of carbamoylation. Herein, treatment of proteins following the protocol by Angel and coworkers induced the strongest shift of the isoelectric point of BSA followed by heating of BSA at 96° C. in urea for 60 min or heating of BSA at 96° C. in urea for 30 min. In addition, heating of BSA in urea at 96° C. for 60 min resulted in the occurence of 2 two forms of partially carbamyolated BSA proteins.

EXAMPLE 4: INFLUENCE OF THE pH VALUE ON THE CARBAMOYLATION OF BSA BY TREATMENT WITH A 2 M UREA SOLUTION

In this experiment, bovine serum albumine (BSA; 1 mg/mL in H$_2$O) was mixed 1:1:1 (vol/vol/vol) with a 6 M urea solution and 30 mM Tris pH 3.9 or 30 mM Tris pH 6.8 or 30 mM Tris pH 8.7 or alternatively BSA (1 mg/mL in H$_2$O) was mixed 1:1:1 (vol/vol/vol) with H$_2$O and 30 mM Tris pH 3.9 or 30 mM Tris pH 6.8 or 30 mM Tris pH 8,7. Then the samples were incubated for 2 hours at 96° C. on a thermoshaker (300 rpm) and separated by 10% SDS-PAGE. Proteins were visualized by staining with Coomassie brilliant blue.

These experiments showed that the chemical modification (partial carbamoylation) of BSA observed after treatment with 2 M urea, 10 mM Tris for 2 h at 96° C. is not substantially influenced by the pH value, ranging from pH 3.9 to pH 8.7.

EXAMPLE 5: ROLE OF THE INCUBATION TIME IN UREA-MEDIATED CARBAMOYLATION OF BSA

BSA (1 mg/mL in H$_2$O) was mixed 1:1:1 (vol/vol/vol) with 6 M urea and 30 mM Tris pH 3.9 and incubated for 0 to 60 minutes (0, 2, 3, 4, 5, 20, 30, 45, 60 min) at 96° C. In an independent experiment BSA was mixed 1:1:1 (vol/vol/ vol) with 6 M urea and 30 mM Tris pH 3,9 and incubated for 0 to 8 hours (0, 0.5, 0.75, 1, 1.5, 2, 2.5, 3, 4, 5, 6, 7, 8 hours) at 96° C. Then, the samples were separated by 10% SDS- PAGE and proteins were visualized by staining by means of Coomassie brilliant blue staining.

These experiments showed that treatment of BSA with 6 M urea and 30 mM Tris pH 3.9 at 96° C. resulted in a time dependent increase in the extend of BSA carbamoylation, as shown by a decelerated sedimentation of the modified BSA proteins in SDS polyacrylamide gels. Herein a detectable increase in the molecular mass of BSA was observed already after 2 to 3 minutes of incubation. An increase in the molecular mass of BSA was observed up to 2 hours of incubation. At later time points urea-treatment of BSA at 96° C. resulted in reduced quantities of detectable BSA protein, strongly suggesting an increased degradation of modified BSA.

EXAMPLE 6: INFLUENCE OF THE INCUBATION TEMPERATURE IN UREA-MEDIATED CARBAMOYLATION OF BSA

BSA (1 mg/mL in $H_2O$) was mixed 1:1:1 (vol/vol/vol) with 6 M urea and 30 mM Tris pH 3.9 and incubated for 2 hours at temperatures ranging from 0 to 96° C. (0, 4, 18, 30, 40, 50, 60, 70, 80, 90, 96° C.). Then, samples were separated by 10% SDS-PAGE and proteins were visualized by staining by means of Coomassie brilliant blue staining.

At the described test conditions, a detectable carbamoylation of BSA was seen at incubation temperatures greater than 60° C.

EXAMPLE 7: MODULATION OF THE ISOELECTRIC POINT OF THE HUMAN CYTOMEGALOVIRUS (CMV) IE1 PROTEIN BY TREATMENT WITH DEPOSED UREA (HEATED FOR MORE THAN 1 HOUR AT 96° C., THEN INCUBATED FOR 7 TO 14 DAYS AT ROOM TEMPERATURE)

Either 100 µl IE1 protein (0.89 µg/ml in phosphate-buffered saline (PBS) (Lonza)) or IE1 (in PBS) mixed up 1:1 (vol/vol) with 8 M deposed urea (heated for more than 1 hour at 96° C., then incubated for 7 to 14 days at room temperature) were incubated over night at 40° C. Then, proteins were separated by isoelectric focusing on IEF strips (Immobiline™ DryStrip pH 3-10, 13 cm, GE Healthcare) at 37500 Vh followed by a 10% SDS-PAGE. Proteins were visualized by silver staining.

The results of these experiments show, that incubation with deposed urea induces chemical modifications lowering the isoelectric point of CMV IE1.

EXAMPLE 8: MALDI-TOF MS ANALYSIS OF UNTREATED AND CARBAMOYLATED BSA

For the preparation of the MALDI-TOF-Target the dried droplet method was used. Therefore, polypeptides were dissolved in buffer (50% acetonitrile (ACN), LC/NS grade (J. T. Baker), 0.01% trifluor acetic acid (TFA), polypeptide sequencing grade (Applied biosystems) and then dissolved directly with the matrix solution comprising a-cyano-4-hydroxycinnamic acid at a matrix to sample ratio of 1:1 to 10:1. Subsequently, 1 µl matrix-sample mixture was applied onto the sample plate, dried at room temperature and analyzed using a MALDI TOF 4800 plus Analyzer from Applied Biosystems. The mass spectra were recorded on a reflector Bruker reflex V delayed extraction MALDI-TOF mass spectrometer equipped with a 2 GHz LeCroy digitizer and 337 nm N2laser using the following parameters: positive polarity, acceleration voltage 20 kV; IS/2 17 kV; focusing lens voltage 8.90 kV; extraction delay 400 ns. The detector was gate. Typically 100 shot were accumulated from three to five different positions within a sample spot. Protein identifications were obtained using MASCOT (MatrixScience) and by searching for matching peptide mass fingerprints in a protein database. The search criteria used were fix modification carboxamidomethylation of cysteine, variable modification methionine oxidation and considered the accuracy of the experimental to theoretical pI and molecular weight. Protein scores are significant when p value is smaller than 0.05 (p value is the probability that the observed match is a random event).

Spectra were obtained from unmodified BSA; double-isotopic protonated mass 33230.3 and BSA after mixture (1:1; vol/vol) with deposed 8 M urea (heated for more than 1 hour at 96° C., then incubated for 7 to 14 days at room temperature); double-isotopic protonated mass 33497. Thus, at these reaction conditions urea treatment of BSA induced a mass shift of 226.7 Dalton corresponding to 12.4±2 carbamoylations.

EXAMPLE 9: ANALYSIS OF POLYPEPTIDE CARBAMOYLATION BY NUCLEAR MAGNETIC RESONANCE (NMR) SPECTROSCOPY

With unlabelled protein the usual procedure is to record a set of 2D homonuclear NMR experiments: COSY, TOCSY an NOESY. Therefore, 190 µL polypeptide solution, 190 µL PBS (Lonza) and 20 µL standard solution S5 ($D_2O$ plus trimethylsilyl-2,2,3,3-tetradeuteropropionic acid (TSP)) are given in a 5 mm NMR-tube (Norell 502). The samples are mixed homogeneous by gently reversing the closed tube and analyzed by a Bruker AVANCE II+ 600 MHz NMR spectrometer with the following parameter:
Temperature: 283 K (10° C.)
Sample head: TXI
Method: 500-XXX-Lif600-TXI-V1
NS (transients): 128 (1D-Spectra) bzw. 16 (2D-Spectra)
SWH (spectral window): 9591 Hz (equates 16 ppm)
D1 (time between transients): 2 s

EXAMPLE 10: ROLE OF INCUBATION TEMPERATURE AND THE INCUBATION TIME IN THE UREA-INDUCED CARBAMOYLATION OF BSA

In this experiment BSA (1 mg/mL in $H_2O$) was mixed 1:1 (vol/vol) with either a freshly prepared 4 M urea solution or 4 M urea, which was pretreated for 1 hour at 96° C., then cooled quickly to 40° C. and kept for 10 min at 40° C. Then samples were incubated for either 0, 2, 4 or 17 hours at 40° C. in a thermoshaker (300 rpm). Then proteins were separated by 10% SDS-PAGE and proteins were visualized by staining with Coomassie brilliant blue.

These experiments showed that freshly prepared 4 M urea solution was less efficient than heated urea in the carbamoylation of BSA. In addition, significant increase in the molecular mass of BSA was detectable after 17 hours, but not after 2 and 4 hours of incubation with both freshly prepared and pre-heated urea. Under the described conditions, urea-treated BSA revealed only a weak increase in its molecular mass indicating a partial carbamoylation of BSA.

EXAMPLE 11: CARBAMOYLATION OF BSA BY DEPOSED UREA

BSA (1 mg/mL in $H_2O$) was mixed 1:1 (vol/vol) with deposed 4 M urea (which was pretreated for 1 hour at 96° C. and then incubated for 8 days at room temperature) and then incubated for 0 to 24 hours (0, 2, 4, 6, 8, 10, 24 hours) at 40° C. Then the samples were separated by 10% SDS-PAGE and proteins were visualized by staining with Coomassie brilliant blue.

In these experiments, detectable increase of the molecular mass of BSA was observed at hour 24, but not at hours 2 to 10 of incubation with deposed urea.

EXAMPLE 12: CHEMICAL MODIFICATION (CARBAMOYLATION) OF BSA WITH DEPOSED UREA RESULTS IN MODIFIED BSA PROTEINS REVEALING AN ALTERED $pK_I$ VALUE

BSA (1 mg/mL in $H_2O$) was mixed 1:1:1 (vol/vol/vol) with $H_2O$/HCl (pH 3.6) and 30 mM Tris pH 3.6 or with 6 M urea-solution and 30 mM Tris pH 3.6 and samples were incubated for 0 min, 30 min or 60 min at 96° C. Alternatively 10 mM BSA was mixed 1:1 (vol/vol) with 4 M deposed urea (heated 1 hour at 96° C., then kept for 3 month at room temperature) and incubated 20 hours at 40° C. Then, proteins were separated by isoelectric focusing on IEF strips (Immobiline™ DryStrip pH 3-10, 11 cm, GE Healthcare) at 26350 Vh followed by a 10% SDS-PAGE and proteins were visualized by silver staining.

These experiments demonstrate that both heating of urea/BSA mixtures and incubation of BSA with deposed urea resulted in a modified BSA protein revealing an altered isoelectric point. At the described conditions heating of BSA/urea mixtures at 96° C. resulted in a stronger reduction of the isoelectric point when compared to the incubation of BSA with deposed urea at 40° C. In addition, the elongated heating of BSA/urea mixtures resulted in a continuous lowering of the isoelectric point of BSA, indicating an increased carbamoylation of BSA.

EXAMPLE 13: CHEMICAL CARBAMOYLATION OF BSA BY TREATMENT WITH POTASSIUM CYANATE

In these experiments, BSA (1 mg/mL in $H_2O$) was incubated for 1 hour at 40° C. with either 25, 100, 500 or 1000 mM potassium cyanate on a thermoshaker (300 rpm). Then, the samples were separated by 12.5 SDS PAGE and visualized by means of Coomassie brilliant blue staining. In these investigations, incubation with potassium cyanate induced a significant increase of the molecular mass of BSA by carbamoylation.

EXAMPLE 14: CHEMICAL CARBAMOYLATION OF BSA BY TREATMENT WITH POTASSIUM CYANATE

In these experiments, BSA (1 mg/mL in $H_2O$) was incubated for 19.5 hour at 40° C. with either 0 mM, 1 mM, 5 mM, 10 mM, 20 mM, 50 mM, 100 mM, 200 mM or 500 mM potassium cyanate on a thermoshaker (300 rpm). Then, the samples were separated by 10% SDS PAGE and visualized by means of Coomassie brilliant blue staining. In these investigations, incubation with potassium cyanate induced a significant increase of the molecular mass of BSA by carbamoylation.

EXAMPLE 15: PRODUCTION AND PURIFICATION OF THE HUMAN CYTOMEGALOVIRUS (CMV) IE1 PROTEIN IN E. COLI

In order to produce human Cytomegalovirus IE1 protein, the plasmid pGEX-KG-IE1 was transformed into the *E. coli* strain M15[pRep4]. For the construction of pGEX-KG-IE1, the gene encoding the IE1 protein was excised from plasmid pcDNA-IE1 using the restriction enzymes HindIII/EcoRI and treated with the Klenow enzyme. Obtained fragment was then cloned into the SmaI/EcoRI digested plasmid pGEX-KG, which was treated with alkaline phospatase, prior to ligation to avoid self annealing of the vector. For the generation of pcDNA-IE1 the coding region of the IE1 protein was excised with KpnI/BamHI from plasmid pCGN-IE1 (Nevels et al. (2004), *J. Virol.* 78:7803) and inserted into the KpnI/BamHI digested plasmid pcDNA3 (Invitrogen). All cloning steps were performed as essentially described in the laboratory manual "Molecular cloning: A laboratory manual, third edition (Sambrook et al. (2001), Cold Spring Harbor Laboratory, New York).

The pRep4 plasmid encodes a repressor of the lac promoter ($lacI^q$) and thus allows an almost complete repression of the protein production by pGEX-expression vectors in the absence of the inducer of protein expression. For the production of CMV IE1, over night cultures of pGEX-KG-IE1 transformed *E. coli* strain M15[pRep4] were diluted in $LB_{amp/kana}$ medium and the expression of IE1 was induced for 16 hours with 1 mM isopropyl thiogalactoside (IPTG). Induced cells produced increased levels of IE1 proteins with molecular weights of approximately 80 and 32 kDa, corresponding to that of the glutathione S transferase (GST)-IE1 and GST proteins and additional proteins with a lower molecular weight, representing degradation products of the GST-IE1 and GST protein. The identity of these proteins was confirmed by immunoblotting using an IE1 specific mouse anti-CMV IE1 monoclonal antibody ((clone 1B12) (Zhu et al. 1995, *J. Virol.* 69: 7960). Therefore, M15[pRep4] cells were transfected with plasmid pGEX-KG-IE1 and aliquots of the cells were lysed prior to and after 16 hours of IPTG induction. Then cell lysates were subjected to a 10% SDS-PAGE and separated proteins were transferred to nitrocellulose. Then, IE1 proteins were visualized using an anti-IE1 monoclonal antibody (clone 1B12). Separation of proteins by SDS PAGE and subsequent analysis of proteins by immunoblotting was performed as described in the laboratory manual "Molecular cloning: A laboratory manual, third edition (Sambrook et al. (2001), Cold Spring Harbor Laboratory, New York).

For the purification of IE1 proteins pGEX-KG-IE1 transformed M15[pRep4] cells were sedimented after 16 hours of IPTG induction by centrifugation for 10 min at 11000 rpm in a Eppendorf Centrifuge 5417R and the pellet was resuspended in PBS (Lonza) without bivalent ions (140 mM NaCl, 2.7 mM KCl, 10 mM $Na_2HPO_4$; 1.8 mM $KH_2PO_4$). In addition, a protease inhibitor cocktail (complete, Roche, 1 tablet in 50 mL PBS (Lonza)) was added to prevent protein degradation. Then, cells were completely lysed using a french press (1.5 kbar, 4° C.) and cell debris were sedimented by centrifugation (15000 rpm, 30 min, 4° C. in a Sorvall SS34 rotor). The soluble fraction of the cell lysate including the GST-IE1 fusion protein was then purified using a GST column. Herein, the enrichment of the GST-IE1 fusion protein was achieved by binding to Glutathione Sepharose™ and subsequent elution with reduced glutathione (50 mM Tris/HCl, 10 mM reduced glutathione, pH 8.5). The eluate was collected in 2 mL fractions and the protein content was determined in each fraction by measuring the optical density at 280 nm. The protein containing fractions were analysed by 12.5 SDS PAGE and visualized by means of Coomassie brilliant blue staining. Fractions, containing the GST-IE fusion protein were combined and incubated for three hours with thrombin (7 U/mg GST-IE1 fusion protein) to separate the GST tag. Then, IE1 was separated from GST-IE1 fusion proteins by anion exchange chromatography using HQ-Poros® columns (Applied Biosystems). Herein, GST and IE1 show striking differences in its isoelectric points (GST: 6.52; TEL 4.58). While GST is not binding to the column and can be detected in the flow through, IE1 is binding and can be eluated from the column with 540 mM NaCl using a linear NaCl gradient (50 mM to 1 M). The eluate was collected in 2 mL fractions and the protein content in each fraction was determined by measuring the optical density at 280 nm. The protein containing fractions were analysed by 12.5 SDS PAGE and staining with Coomassie Brilliant Blue. Fractions, containing the IE1 protein were combined. For the separation of residual GST-IE1 fusion proteins combined antigens were subjected to a second separation on a GST column. Herein, GST-IE1 binds to the Glutathione Sepharose™ matrix, whereas IE1 is not binding and can be detected in the flow through. In order to analyse the purity and identity, obtained IE1 was subjected to a 12.5 SDS-PAGE and the gel was analysed by staining with Coomassie brilliant blue. In addition, proteins were transferred from separate gels to nitrocellulose and IE1 proteins were specifically visualized by immunoblotting using an IE1-specific monoclonal antibody (clone 1B12).

Obtained IE1 protein revealed a purity of >90%. The protein was concentrated using Amicon concentration devices and filters with a cut-off of 25 kDa. The concentration of purified IE1 was determined by determining the molar extinction coefficient. Herein, an $OD_{280}$ value of 21500 relates to 1 mol of the IE1 protein. 4 to 8 mg purified IE1 were obtained from 1 L culture broth.

EXAMPLE 16: CAPACITY OF CARBAMOYLATED IE1 PROTEIN AND YIL PEPTIDE TO SPECIFICALLY REACTIVATE CD4$^+$ AND/OR CD8$^+$ T CELLS

Here the suitability of carbamoylated IE-1 protein and YIL peptide to be presented on MHC molecules of classes I and II and subsequently the ability to reactivate polypeptide-specific CD4$^+$ and CD8$^+$ T cells was analyzed by means of flow cytometry. This is based on the observation that almost all HLA A2-positive, CMV-positive blood donors possess CD8$^+$ cytotoxic T cells which recognise a specific epitope (YILEETSVML (SEQ ID NO:4); amino acid 315-324), (Prod'homme et al. (2003), *J. Immunol.* 170:2030) within the CMV protein IE1. For control, samples were stimulated with the peptide E10F, covering a murine CTL epitope within the p24 capsid region of HIV-1$_{(BH10)}$ Gag (aa291-300) (Wild et al. (2004) *Vaccine.* 2004; 22:1732-1743).

Therefore heparinised whole blood of a seropositive donor was incubated in aliquots of 1 ml in sterile Falcon tubes (BD) with not modified and carbamoylated IE-1 protein and YIL peptide. For carbamoylation purified IE1 protein (0.89 µg/mL in PBS(Lonza)) or purified YIL peptide were mixed 1:1 (Vol/Vol) with 8 M deposed urea (preincubated over night at 96° C.) and incubated over night at 40° C. The following stimulations were then carried out:

1: control peptide: not modified HIV Pr55$^{gag}$ derived peptide (10 µg/ml)
2: not modified IE1 protein (10 µg/mL)
3: carbamoylated IE1 protein (10 µg/mL)
4: not modified IE1 derived peptide YIL (10 µg/mL)
5: carbamoylated IE1 derived peptide YIL (10 µg/mL)

In addition to the proteins or peptides monoclonal antibodies against the costimulatory molecules CD28 and CD49d (Becton Dickinson) were added in a final concentration of 1 µg/mL. The cells were then incubated at 37° C. for 2 hours. Then, 10 µg/mL Brefeldin A were added to the samples to prevent cytokine secretion. The samples were then thoroughly vortexed and incubated at 37° C. for further 7 hours.

After 9 hours of incubation 100 µl of ice-cold EDTA solution (EDTA in PBS (Lonza), 20 mM) were added. The samples were briefly vortexed and then incubated for 10 minutes at room temperature. The samples were then thoroughly vortexed and incubated with 9 ml FACS lysing solution (BD) for 10 minutes at room temperature. The samples were then centrifuged at 4° C. for 8 minutes at 340 g. The supernatant was carefully decanted and the cells were washed twice with 9 ml FACS buffer (PBS (Lonza)+0.1% w/v NaN$_3$+1% w/v FCS). The cells were then resuspended in a small volume of FACS buffer for staining surface molecules. Therefore, fluorochrome conjugated monoclonal antibodies against surface molecules (CD3 FITC, CD4 ECD and CD8 APC) were added according to the manufacturer's protocol and incubated at room temperature for 20 min in the dark. The cells were then washed with FACS buffer as previously described, fixed through adding of 0.5 ml 2% paraformaldehyde (2% in PBS (Lonza)) and incubated for 10 min in the dark. The cells were then transferred to FACS tubes (BD) and washed with 3 ml FACS buffer. Next the permeabilisation and intracellular staining were carried out. Herefore 10 µl of permeabilising solution (2 Saponine in PBS) and the flurochrome conjugated monoclonal IFN-γ-PE antibody (according to the manufacturer's protocol) were pipetted onto the cells. The samples were thoroughly vortexed and incubated for 30 minutes at room temperature in the dark. The cells were then washed twice with 3 ml 0.1% Saponine-solution (0.1% Saponine in PBS (Lonza)) and fixed in 0.5 ml paraformaldehyde (1% in PBS (Lonza)). Stained cells were run on a FACS Epics XL MCL flow cytometer (Beckman Coulter) and the results were evaluated using the CellQuest Software (Becton Dickinson).

The results show that significantly more CD3 and CD8 expressing cells can be retrieved by the stimulation with carbamoylated polypeptides.

EXAMPLE 17: CAPACITY OF UREA- AND CYANATE-CARBAMOYLATED PEPTIDES TO SPECIFICALLY REACTIVATE CD8$^+$ T CELLS

The ability of carbamoylated peptides to reactivate peptide-specific CD8$^+$ T cells was analyzed using flow cytometric analysis of intracellular IFN-γ production after peptide-specific incubation. Therefore whole blood was incubated with different formulations of the YIL peptide for 9 hours and PBMC were stained according to the protocol already described in Example 16. In these experiments the YIL peptide (10 µg/µl in 100% DMSO) was mixed 1:1 (Vol/Vol) either with 8 M deposed urea (preincubated over night at 96° C.) or 200 mM KOCN and incubated over night at 40° C. The following stimulations were then carried out:
1: 10 μg/mL control peptide HIV p24 derived peptide E10F
2: 10 μg/mL CMV IE1 derived peptide YIL
3: 10 μg/mL CMV IE1 derived peptide YIL carbamoylated with 100 mM KOCN (including a final concentration of 200 μM KOCN in the stimulated blood sample)
4: 10 μg/mL CMV IE1 derived peptide YIL carbamoylated with 4 M urea (including a final concentration of 8 mM urea in the stimulated blood sample)
5: 200 μM KOCN (final concentration in the stimulated blood sample)
6: 8 mM urea (final concentration in the stimulated blood sample)

The results show that with 200 mM KOCN carbamoylated YIL peptide reactivates significantly more CD8+ T cells than the non carbamoylated YIL peptide.

EXAMPLE 18: CAPACITY OF CYANATE-CARBAMOYLATED PEPTIDES AND PROTEINS TO SPECIFICALLY REACTIVATE CD8+ T CELLS

In this experiment the capacity of cyanate-carbamoylated CMV YIL peptide and pp65 protein to specifically reactivate CD8+ T cells was analyzed. Therefore whole blood was incubated with different formulations of the YIL peptide for 6 hours and PBMC were stained according to the protocol already described in Example 16. In these experiments, the YIL peptide (2 μg/μl in 100% DMSO) was mixed 1:1 (Vol/Vol) with either 200 mM, 400 mM or 1000 mM KOCN in $H_2O$ and incubated over night at 40° C. The immunodominant region of CMV (strain AD169) pp65 (aa 862-1048; RecMol UL83-Pp65, Cat. No 1B023A) was dissolved in $H_2O$ including 140 mM NaCl, 2.7 mM KCl, 10 mM $Na_2HPO_4$, 1.8 mM $KH_2PO_4$ as well as different concentrations of KOCN ranging from 0 to 500 mM and incubated over night at 40° C. The following stimulations were carried out:
1: non stimulated cells (negative control)
2: 10 μg/mL CMV IE1 peptide YIL
3: 10 μg/mL CMV IE1 peptide YIL carbamoylated with 100 mM KOCN (including a final concentration of 1 mM KOCN in the stimulated blood sample)
4: 10 μg/mL CMV IE1 peptide YIL carbamoylated with 200 mM KOCN (including a final concentration of 2 mM KOCN in the stimulated blood sample)
5: 10 μg/mL CMV IE1 peptide YIL carbamoylated with 500 mM KOCN (including a final concentration of 5 mM KOCN in the stimulated blood sample)
6: 10 μg/mL CMV pp65 protein (immunodominant region)
7: 10 μg/mL CMV pp65 protein carbamoylated with 100 mM KOCN (including a final concentration of 1 mM KOCN in the stimulated blood sample)
8: 10 μg/mL CMV pp65 protein carbamoylated with 200 mM KOCN (including a final concentration of 2 mM KOCN in the stimulated blood sample)
9: 10 μg/mL CMV pp65 protein carbamoylated with 500 mM KOCN (including a final concentration of 5 mM KOCN in the stimulated blood sample)

The results show that potassium cyanate carbamoylated YIL peptide and pp65 protein in presence of 0.04 M urea reveal an increased capacity to specifically reactivate CD8+ T cells than the non carbamoylated YIL peptide and pp65 protein, respectively. Herein, treatment of pp65 with increasing concentrations of potassium cyanate ranging from 100 to 500 mM directly correlates with an increasing capacity of pp65 to specifically activate CD8+ T cells for IFN-γ production. In contrast—for the YIL peptide—pretreatment with 100 mM and 200 mM potassium cyanate is more efficient to increase the potency of YIL to specifically stimulate CD8+ T cells than pretreatment of YIL with 500 mM potassium cyanate.

EXAMPLE 19: CAPACITY OF UREA-MODIFIED HIV P24 CAPSID ANTIGEN IN COMBINATION WITH CpG ODN 1668 TO ACTIVATE HIV P24-SPECIFIC CD8+ T CELLS IN MICE

The capacity of carbamoylated HIV p24 capsid protein to stimulate p24-specific CD8+ T cells was analyzed in the BALB/c mouse model. Therefore, an aliquot of purified recombinant p24 was treated over night at 40° C. with deposed urea (pre-heated for 1 hour at 96° C.) and then extensively dialysed against 0.04 M urea in PBS (Lonza). Six female BALB/c mice at an age of 40 to 60 days were immunised intramuscularly with either 10 μg non modified p24 in absence (group 4) or presence of 50 μg/dose CpG ODN1668 (group 5) or urea-treated, modified p24 (up 24) in absence (group 2) or presence of 50 μg/dose CpG ODN1668 (group 3). The immunogens were administered in a total volume of 100 μg in PBS (Lonza). For controls, groups of six mice were immunized with either 0.04 M urea solution (group 1) or 10 μg HIV insect cell-derived HIV Gag virus-like particles (VLP) (Deml et al. 2005, *Mol. Immunol.* 42:259) in a total volume of 100 μl in PBS (Lonza). All animals were immunized at week 0 and received a booster injection with the same immunogens at weeks 2 and 4. At weeks 3 and 6, three mice of each group were sacrified by cervical dislocation and spleens were removed aseptically.

Then spleens were placed in 50 ml Falcon tubes (B D Heidelberg, Germany) containing 10 ml splenocyte medium (RPMI medium, 5% heat-inactivated fetal calf serum (FCS), 20 mM HEPES, 50 μM 2-mercapto-ethanol, 1% Pen/Step solution) and kept at room temperature (not longer than 15 min). Medium was replaced by the same volume of fresh splenocyte medium and spleens were transferred onto a 70 μM cell strainer (BD cat. No. 352350), which was placed on a 50 ml Falcon tube. Single cell suspensions were generated by grinding the spleen against the cell strainer with the plunger of a 5 ml syringe until mostly fibrous tissue remained left. Singularized cells were aspirated from the cell strainer by repeatedly adding 2 ml splenocyte medium. Obtained cell suspensions were sedimented by centrifugation at 300 g for 5 min at room temperature and pelleted cells were resuspended in 5 mL/spleen ACK hemolysis buffer (150 mM $NH_4Cl$, 1 mM $KHCO_3$, 0.1 mM $Na_2EDTA$ (Titriplex III); adjust pH 7.2 to 7.4 with 1 N HCl) by gently but thoroughly pipetting with a 10 mL or 25 mL plastic pipet. Then, cell suspension was centrifuged at 300 g for 5 min at room temperature and washed three times with 10 mL/spleen splenocyte medium. At each washing step the cell suspension was separated from aggregated fibrous tissue. Finally, cells were resuspended in 5 ml/spleen splenocyte medium, counted and adjusted to a final concentration of $2 \times 10^6$ cells/ml in splenocyte medium and preserved at 37 C.° (not longer than 30 min) until use.

$2 \times 10^6$ murine splenocytes were cultured in 100 μl splenocyte medium per well on a flat bottom 96 well plate at 37° C. Cells were stimulated with 10 μg of either HIV C-type p24 peptide (AMQILKDTI (SEQ ID NO: 1); $aa_{197-205}$ in case of p24 immunized mice) or the $HIV_{LAI}$ A9I peptide (AMQMLKETI (SEQ ID NO: 2); aa 197-205 (Wild et al. (2004), *Vaccine* 22:1732) in case of VLP-stimulated mice) or for negative control with an irrelevant peptide representing an HLA A2-restricted CTL epitope within the human prostate specific antigen (PSA 141-150 FLTPKKLQCV (SEQ ID NO: 3); Chakraborty et al. (2003), *Cancer Immunol. Immunother.* 52:497). A combination of PMA (phorbol 12-myristate 13-acetate) and Ionomycin served as positive control. Each polypeptide stimulation was performed as duplicate.

Stimulator immunogens were mixed as follows:
negative control: 1.5 ml spenocyte medium+3 μl Brefeldin A (5 μg/μl)+3 μl PSA-peptide (10 μg/μl)
positive control: 1 ml spenocyte medium+2 μl Brefeldin A (5 μg/μl)+1 μl PMA (1 μg/ml)+1 Ionomycin (1 μg/μl)
HIV C-type p24 peptide solution: 1.5 ml spenocyte medium+3 μl Brefeldin A (5 μg/μl)+3 μl peptide (10 μg/μl)
$HIV_{LAI}$A9I peptide solution: 0.5 ml spenocyte medium+1 μl Brefeldin A (5 μg/μl)+ peptide (10 μg/μl)

The plates were then incubated in a standard incubator at 37° C. After 6 hours the samples were transferred into FACS tubes containing 1 ml FACS buffer (PBS (Lonza), 1% (v/v) FCS, 0.1% w/v $NaN_3$). The samples were then centrifuged at 4° C. for 5 minutes at 300 g. The supernatant was then carefully decanted and the cells were washed again with 1 ml FACS-buffer and centrifuged again at 300 g for 8 minutes. The cells were then resuspended in a small volume (approximately 100 μl) of FACS buffer and first incubated for 10 min at 4° C. with anti-FcRII/III mAb (PharMingen, Hamburg, Germany) to block unspecific binding of fluorescence conjugated antibodies. Then surface markers were stained for 30 minutes on ice in a staining volume of 100 μl using the following antibodies according to the manufacturer's protocol: CD3 FITC, CD4 PerCP and CD8 APC. The cells were then washed with 5 ml FACS buffer and centrifuged for 5 minutes at 300 g. After that the cells were fixed with 250 μl Cytofix/Cytoperm (4% (w/v) PFA+1% (w/v) saponine) for 20 minutes on ice. The cells were then washed twice with 5 ml perm/wash (0.1% (w/v) saponine in PBS (Lonza)) and centrifuged for 5 minutes at 500 g at 4° C. after each washing step. The cells were resuspended in 100 μl perm/wash and intracellular IFN-γ was stained using an IFN-γ-PE antibody according to manufacturer's protocol for 20 minutes on ice in the dark. Subsequently, the cells were washed twice with 5 ml FACS buffer and centrifuged for 5 minutes at 300 g after each washing step. Finally the cells were resupended in 200 μl of a 1% paraformaldehyde (PFA) solution. FACS analysis was performed on a FACSCalibur flow cytometer (Becton Dickinson, Germany), acquiring 30,000 $CD8^+$ T cells per sample. FACS data were then analyzed using the CellQuest software.

The results clearly demonstrate that immunization of mice with carbamyolated p24 in combination with CpG ODN 1668 induces significantly more $CD8^+$ T cells in comparison to mice immunized with non modified p24 in absence and presence of CpG ODN 1668 or carbamoylated p24 in absence of CpG ODN 1668.

EXAMPLE 20: UPTAKE OF HIV P24 CAPSID PROTEIN IN MATURE DENDRITIC CELLS

To determine whether HIV p24 capsid protein has an intrinsic property to enter the cytosol of mature dendritic cells and thus whether it has to be classified into the first or the second group of polypeptides as described above the following test has been performed:

$6-9 \times 10^5$/ml mature dendritic cells in R10 (RPMI 1640, 10% human AB Serum) were incubated with 10 μg/ml recombinant HIV p24 capsid protein for 15 min at 37° C. Subsequently, 333 μl of the cell suspension were placed onto a cytospin slide (Hettich, Tuttlingen) and the slide was centrifuged for 3 min at 300 g. After drying the slides for 60 min, the cells were covered with paraformaldehyde (4% in PBS) for fixation and incubated for 15 min at 37° C. The cells were then washed three times with 10 ml PBS. The area were the cells were fixed was then encircled with Vaseline. Then the cytoplasmic membrane of the cells was dyed with 150 μl (5 μg/ml) of an Alexa Fluor dye (Invitrogen, USA) for 10 min. After the slides were washed twice with 10 ml PBS, the cells were covered with 4° C. cold acetone in order to permeabilise the cells. The cells were then saturated with 150 μl R10 for 30 min. After removal of R10 the p24 detection fluorescent antibody KC57-FITC (Coulter Clone, USA) was given onto the cells for 2 hours according to the manufacurer's protocol. The slides were then washed three times with 10 ml PBS. Afterwards, the cell nucleus was marked with 150 μl (10 ng/ml) 4', 6 Diamino-2-phenylindol (DAPI) (Roche, Mannheim). The slide was then washed with 10 ml PBS and dried for 60 min. 15 μl of MobiGlow mounting medium (MoBiTec, Gottingen) was then given on the slide and covered with a cover slip.

The fluorescence microscopy was then performed using a LEICA-DMRX microscope (Leica, Wetzlar). The results were interpreted using the Image-Pro Plus 6.2 software (MediaCybernetics, USA). The microscopic pictures indicated, that HIV p24 capsid protein does not enter the cytosol of the dendritic cells. Thus, HIV p24 capsid protein is a polypeptide according to the second group of polypeptides as described above.

The invention claimed is:

1. A method for priming, expansion and/or reactivation of polypeptide-specific T cells comprising the following steps:
   a) incubating polypeptides in a solution comprising cyanate ions, wherein the cyanate ions are present at a concentration in the range from about 1 to about 1000 mmol/l, and
   b) incubating cells with the polypeptides of step a) in the presence of urea and in absence or presence of immune-modulatory substances.

2. The method according to claim 1, wherein the cyanate ions are present at a concentration in the range from about 5 mmol/l to about 900 mmol/l, from about 10 mmol/l to about 800 mmol/l, from about 20 mmol/l to about 700 mmol/l, from about 50 mmol/l to about 600 mmol/l or from about 100 mmol/l to about 500 mmol/l.

3. The method according to claim 1, wherein the solution of step a) comprises additionally urea, preferably in the range from about 0.01 mol/liter to about 8 mol/liter, from about 0.1 to about 0.5 mol/liter, from about 0.5 to about 5 mol/liter, or from about 5 to about 8 mol/liter.

4. The method according to claim 3, wherein the urea has been pretreated by incubation.

5. The method according to claim 1, wherein the urea concentration in step b) is in the range from about 0.001 to about 0.8 mol/l, from about 0.01 to about 0.1 mol/l, from about 0.015 mol/l to about 0.09 mol/l, from about 0.02 mol/l to about 0.08 mol/l, from about 0.025 mol/l to about 0.07 mol/l, from about 0.03 mol/l to about 0.06 mol/l or from about 0.035 mol/l to about 0.05 mol/l and in particular wherein the urea concentration in step b) is about 0.04 mol/l.

6. The method according to claim 3, wherein the urea solution additionally contains NaCl with a concentration in the range from about 0.25 mmol/l to about 200 mmol/l, or from about 0.25 mmol/l to about 75 mmol/l and/or DTE or DTT with a concentration in the range from about 0.25 nmol/l to about 200 nmol/l, or from about 0.25 nmol/l to about 75 nmol/l.

7. The method according to claim 1, wherein the polypeptides in:
   (i) step a) are present in a concentration in the range from about 0.1 to about 50 µg/ml, from about 1 to about 40 µg/ml, from about 3 to about 30 µg/ml, or from about 5 to about 20 µg/mL and in particular in a concentration of about 10 µg/ml; and/or
   (ii) step b) are present in an amount in the range from about 0.1 to about 200 µg or higher, or from about 0.1 to about 200 µg, or from about 0.1 to about 2 µg, or from about 0.1 to about 10 µg, or from about 10 to about 50 µs or from about 50 to about 200 µg for approximately $10^6$ cells.

8. The method according to claim 3, wherein the incubation of the polypeptides in step a) results in an increase of the molecular weight of the polypeptides and/or a shift of the $pK_i$-value of the polypeptides to a more acidic $pK_i$-value.

9. The method of claim 3, wherein the urea is in the range from about 0.01 mol/liter to about 8 mol/liter, from about 0.1 to about 0.5 mol/liter, from about 0.5 to about 5 mol/liter, or from about 5 to about 8 mol/liter.

10. The method according to claim 4, wherein the urea has been pretreated by heat and/or time.

11. The method of claim 1, wherein the polypeptide-specific T cells are preferably $CD4^+$ T cells and/or $CD8^+$ T cells.

12. The method of claim 1, wherein the immune cells are from a subject undergoing therapeutic or prophylactic vaccination.

13. The method of claim 1, wherein the immune cells are from a subject undergoing therapeutic treatments of diseases involving immune cells.

14. The method of claim 1, wherein the immune cells are from a subject undergoing therapeutic treatment with a medicament that causes deletion or anergy of immune cells.

15. The method of claim 1, wherein the immune cells are from a subject suspect of having or afflicted with a disease induced by micro-organisms and parasites involving immune cells.

16. The method of claim 1, wherein the immune cells are from a subject suspected of having afflicted with chronic inflammation involving immune cells.

17. The method of claim 1, wherein the immune cells are from a subject suspected of having tumor-antigen-specific immune cells or afflicted with cancer.

18. The method of claim 1, wherein the immune cells are from a subject undergoing transplant.

19. The method of claim 1, wherein the immune cells are from a subject suspected of having or afflicted with auto-immune disease.

20. The method of claim 1, wherein the immune cells are from a subject undergoing selection as a blood donor.

21. The method of claim 20, wherein said selection is for vaccine trial candidacy.

22. The method of claim 20, wherein said selection is for candidacy in the testing of therapeutic treatments.

* * * * *

UNITED STATES PATENT AND TRADEMARK OFFICE
CERTIFICATE OF CORRECTION

PATENT NO. : 9,850,464 B2  
APPLICATION NO. : 15/260269  
DATED : December 26, 2017  
INVENTOR(S) : Sascha Barabas et al.

Page 1 of 1

It is certified that error appears in the above-identified patent and that said Letters Patent is hereby corrected as shown below:

In the Claims

In Claim 3, Column 39, Lines 47-50, delete ", preferably in the range from about 0.01 mol/litre to about 8 mol/litre, from about 0.1 to about 0.5 mol/litre, from about 0.5 to about 5 mol/litre, or from about 5 to about 8 mol/litre".

In Claim 7, Column 40, Line 40, delete "µs" and insert --µg-- therefor.

Signed and Sealed this  
Eleventh Day of June, 2019

Andrei Iancu  
*Director of the United States Patent and Trademark Office*

SEQUENCE LISTING

<160> NUMBER OF SEQ ID NOS: 4

<210> SEQ ID NO 1
<211> LENGTH: 9
<212> TYPE: PRT
<213> ORGANISM: Human immunodeficiency virus

<400> SEQUENCE: 1

Ala Met Gln Ile Leu Lys Asp Thr Ile
1            5

<210> SEQ ID NO 2

```
<211> LENGTH: 9
<212> TYPE: PRT
<213> ORGANISM: Human immunodeficiency virus

<400> SEQUENCE: 2

Ala Met Gln Met Leu Lys Glu Thr Ile
1               5

<210> SEQ ID NO 3
<211> LENGTH: 10
<212> TYPE: PRT
<213> ORGANISM: Homo Sapiens

<400> SEQUENCE: 3

Phe Leu Thr Pro Lys Lys Leu Gln Cys Val
1               5                   10

<210> SEQ ID NO 4
<211> LENGTH: 10
<212> TYPE: PRT
<213> ORGANISM: Cytomegalovirus

<400> SEQUENCE: 4

Tyr Ile Leu Glu Glu Thr Ser Val Met Leu
1               5                   10
```